US011326206B2

(12) United States Patent
Zhang et al.

(10) Patent No.: US 11,326,206 B2
(45) Date of Patent: May 10, 2022

(54) METHODS OF QUANTIFYING TARGET NUCLEIC ACIDS AND IDENTIFYING SEQUENCE VARIANTS

(71) Applicant: OMNIOME, INC., San Diego, CA (US)

(72) Inventors: Yi Zhang, San Diego, CA (US); Steven Brentano, San Diego, CA (US); Eugene Tu, San Diego, CA (US); Kandaswamy Vijayan, San Diego, CA (US)

(73) Assignee: PACIFIC BIOSCIENCES OF CALIFORNIA, INC., Menlo Park, CA (US)

( * ) Notice: Subject to any disclaimer, the term of this patent is extended or adjusted under 35 U.S.C. 154(b) by 177 days.

(21) Appl. No.: 16/091,969

(22) PCT Filed: Apr. 6, 2017

(86) PCT No.: PCT/US2017/026376
§ 371 (c)(1),
(2) Date: Oct. 5, 2018

(87) PCT Pub. No.: WO2017/177017
PCT Pub. Date: Oct. 12, 2017

(65) Prior Publication Data
US 2019/0119742 A1    Apr. 25, 2019

Related U.S. Application Data

(60) Provisional application No. 62/319,742, filed on Apr. 7, 2016.

(51) Int. Cl.
C12Q 1/68         (2018.01)
C12Q 1/6858    (2018.01)
(Continued)

(52) U.S. Cl.
CPC ........... *C12Q 1/6858* (2013.01); *C12Q 1/686* (2013.01); *C12Q 1/6827* (2013.01); *C12Q 1/6853* (2013.01)

(58) Field of Classification Search
CPC ....................................................... C12Q 1/68
(Continued)

(56) References Cited

U.S. PATENT DOCUMENTS 8,632,975 B2 * 1/2014 Vander Horn ....... C12N 9/1252
                                                                435/6.12
9,546,398 B2 * 1/2017 Peter .................... C12Q 1/6869
(Continued)

FOREIGN PATENT DOCUMENTS

CN    104830985 A    8/2015
WO    02057491 A2    7/2002
(Continued)

OTHER PUBLICATIONS

Baner et al., "Signal amplification of padlock probes by rolling circle replication", Nucleic Acids Research, Information Retrieval Ltd. vol. 26, No. 22., Nov. 15, 1998, pp. 5073-5078.
(Continued)

*Primary Examiner* — Aaron A Priest
(74) *Attorney, Agent, or Firm* — Kilpatrick Townsend & Stockton LLP

(57) ABSTRACT

The present disclosure provides compositions, methods and systems for quantifying target sequences and identifying target sequence variants.

20 Claims, 18 Drawing Sheets

Specification includes a Sequence Listing.

(51) Int. Cl.
*C12Q 1/6827* (2018.01)
*C12Q 1/6853* (2018.01)
*C12Q 1/686* (2018.01)

(58) Field of Classification Search
USPC .......................................................... 435/6.1
See application file for complete search history.

(56) References Cited

U.S. PATENT DOCUMENTS

2009/0286245 A1* 11/2009 Bjornson ............. C12Q 1/6869
435/6.18
2013/0165328 A1* 6/2013 Previte ................. C12Q 1/6874
506/2

FOREIGN PATENT DOCUMENTS

WO    WO-2009086353 A1 * 7/2009 ........... C12Q 1/6869
WO        2016019455 A1    2/2016

OTHER PUBLICATIONS

PCT/US2017/026376, "Invitation to Pay Add'l Fees and Partial Search Report", dated Jul. 19, 2017, 15 pages.
PCT/US2017/026376, "PCT Search Report", dated Sep. 25, 2017, 22 pages.
PCT/US2017/026376, "International Preliminary Report on Patentability", dated Oct. 18, 2018, 14 pages.

* cited by examiner

- Z:P non-natural nucleotides (FfAME)

- X:Y non-natural hydrophobic packing nucleotides (Synthorx)

- isoC:isoG nucleotide analogs

SEQUENCE LISTING

```
<160> NUMBER OF SEQ ID NOS: 4

<210> SEQ ID NO 1
<211> LENGTH: 78
<212> TYPE: DNA
<213> ORGANISM: Artificial sequence
<220> FEATURE:
<223> OTHER INFORMATION: Single-stranded DNA template used for circle
      formation
<220> FEATURE:
<221> NAME/KEY: misc_feature
<222> LOCATION: (1)..(78)
<223> OTHER INFORMATION: DNA template used for circle formation

<400> SEQUENCE: 1
gtcctcagtc ccaaaagtct gggcctaggg tgctgcagag gcccagagct tctttttttt     60
ttttccgtct gaagagga                                                  78

<210> SEQ ID NO 2
<211> LENGTH: 17
<212> TYPE: DNA
```

```
<213> ORGANISM: Artificial sequence
<220> FEATURE:
<223> OTHER INFORMATION: Primer for rolling circle amplification
<220> FEATURE:
<221> NAME/KEY: Primer
<222> LOCATION: (1)..(17)
<223> OTHER INFORMATION: Primer for initiating rolling circle
      amplification

<400> SEQUENCE: 2
cttttgggac tgaggac                                                       17

<210> SEQ ID NO 3
<211> LENGTH: 21
<212> TYPE: DNA
<213> ORGANISM: Artificial sequence
<220> FEATURE:
<223> OTHER INFORMATION: Primer for sequencing RCA product
<220> FEATURE:
<221> NAME/KEY: Primer
<222> LOCATION: (1)..(21)
<223> OTHER INFORMATION: Sequencing primer

<400> SEQUENCE: 3
gcttcttttt tttttttccg t                                                  21

<210> SEQ ID NO 4
<211> LENGTH: 12
<212> TYPE: DNA
<213> ORGANISM: Artificial sequence
<220> FEATURE:
<223> OTHER INFORMATION: Example barcode
<220> FEATURE:
<221> NAME/KEY: Barcode
<222> LOCATION: (1)..(12)
<223> OTHER INFORMATION: Example barcode

<400> SEQUENCE: 4
gtcagtcagt ca                                                            12
```

METHODS OF QUANTIFYING TARGET NUCLEIC ACIDS AND IDENTIFYING SEQUENCE VARIANTS

RELATED APPLICATIONS

This application claims the benefit of U.S. Provisional Application No. 62/319,742, filed Apr. 7, 2016. The entire disclosure of this earlier application is hereby incorporated by reference.

TECHNICAL FIELD

The present disclosure relates generally to the field of biotechnology. More specifically, the disclosure concerns compositions, methods, and systems for quantifying nucleic acid target sequences, and identifying target sequence variants.

BACKGROUND

Detection and quantification of target sequences are an important part of biological and medical research. The sequence information is helpful for identifying genes or sequence variants (e.g., single nucleotide polymorphisms (SNPs), mutations) associated with diseases and phenotypes, identifying potential drug targets, and understanding the mechanisms of disease development and progress. Sequence information is also an important part of personalized medicine, where it can be used to optimize the diagnosis, treatment, or prevention of disease.

BRIEF SUMMARY

Provided herein are methods for quantifying a target nucleic acid sequence. The methods include contacting a sample with a capture pair including an upstream capture nucleic acid sequence and a downstream capture nucleic acid sequence, wherein the upstream capture sequence hybridizes to the target sequence upstream relative to the downstream capture sequence, and wherein the 5'-end of the upstream capture sequence and the 3'-end of the downstream capture sequence are separated by a nick or N nucleotides, producing a circular nucleic acid molecule by connecting the 5'-end of the upstream capture sequence and the 3'-end of the downstream capture sequence, wherein the circular molecule includes a barcode, and sequencing the barcode, thereby determining the amount of the target sequence in the sample.

Also provided are methods of identifying a nucleic acid sequence variant and the amount of a target sequence in a nucleic acid sample. The methods include contacting a sample with a capture pair including an upstream capture nucleic acid sequence and a downstream capture nucleic acid sequence, wherein the capture pair is capable of binding to a target nucleic acid sequence surrounding the sequence variant in the sample, wherein the capture pair hybridizes to the target sequence, the 5'-end of the upstream capture sequence and the 3'-end of the downstream capture sequence are separated by a nick or N nucleotides, producing a circular molecule by connecting the 5'-end of the upstream capture sequence and the 3'-end of the downstream capture sequence, wherein the circular molecule includes a barcode; and sequencing the sequence variant thereby identifying the sequence variant; and sequencing the barcode thereby determining the amount of the target sequence in the sample.

Provided are methods of amplifying a target sequence in a sample. The methods include providing a single-stranded circular probe including a sequence complementary to the target sequence, contacting the sample with the single-stranded circular probe to form a hybridized product including the target sequence and the single-stranded circular probe, wherein forming the hybridized product produces a double stranded portion and at least one single stranded portion in the target sequence, contacting the hybridized product with an enzyme having exonuclease activity, wherein the enzyme digests the at least one single-stranded portion in target sequence, and amplifying the circular probe by rolling circle amplification using the digested target sequence as a primer.

Alternative methods of amplifying a target sequence in a sample are provided. The methods include providing a single-stranded circular probe including a sequence complementary to the target sequence, hybridizing a blocked primer to the circular probe to form a partially double-stranded circular probe, wherein the partially double-stranded circular probe includes the sequence complementary to the target sequence in the single-stranded region of the circular probe and a recognition site that can be recognized by an endonuclease, contacting the sample with the partially double-stranded circular probe under conditions to form a hybridized product between the target sequence and the partially double-stranded circular probe, contacting hybridized product with the endonuclease, wherein the endonuclease cleaves the target sequence, and amplifying the circular probe by rolling circle amplification using the cleaved target DNA sequence as a primer.

In one aspect, the disclosure relates to a method for quantifying a target nucleic acid sequence present in a test sample. The method includes the steps of (a) contacting the test sample with a capture pair that includes an upstream capture nucleic acid sequence and a downstream capture nucleic acid sequence, where the upstream capture sequence hybridizes to the target sequence upstream relative to the downstream capture sequence. The 5'-end of the upstream capture sequence and the 3'-end of the downstream capture sequence are separated by a nick or a gap. There also is the step of (b) producing a circular nucleic acid molecule by connecting the 5'-end of the upstream capture sequence and the 3'-end of the downstream capture sequence, where the circular molecule includes a first barcode. There also is the step of (c) performing a nucleic acid amplification reaction using the circular molecule as the template to produce an amplification product. Further, there is the step of (d) quantifying the amplification product by sequencing the first barcode, thereby quantifying the target sequence in the test sample. According to one generally preferred embodiment, the amplification product includes a universal priming sequence, and a sequence complementary to the first barcode. Here, sequencing the first barcode in step (d) can involve hybridizing a universal primer to the universal priming sequence of the amplification product, and then determining the sequence of the amplification product downstream of the universal primer. Preferably, step (d) further involves comparing the result from quantifying the amplification product of step (c) with a result from quantifying a second amplification product that was produced in the nucleic acid amplification reaction, where the second amplification product includes the universal priming sequence and a second barcode (i.e., different from the first barcode). More preferably, the nucleic acid amplification reaction in step (c) involves rolling circle amplification. Still more preferably, the first and second amplification products respectively include sequences that are present on different human chromosomes. Alternatively, when the nucleic acid amplification reaction in step (c) involves rolling circle amplification, comparing the different results in step (d) can involve normalizing one quantified result to the other. Alternatively, when the nucleic acid amplification reaction in step (c) involves rolling circle amplification, the sample can be a blood sample obtained from a human patient. When this is the case, the human patient can be a pregnant female, and the blood sample can include both maternal nucleic acids and fetal nucleic acids. According to another generally preferred embodiment, when the amplification product includes a universal priming sequence and a sequence complementary to the first barcode; and when sequencing the first barcode in step (d) includes hybridizing a universal primer to the universal priming sequence of the amplification product, and then determining the sequence of the amplification product downstream of the universal primer; step (c) can include determining the identity of a next correct nucleotide of the first barcode without incorporation of the next correct nucleotide. In one preferred embodiment, step (c) involves determining with a fluorescently labeled nucleotide the identity of the next correct nucleotide of the first barcode without incorporation of the fluorescently labeled nucleotide. In a different preferred embodiment, step (c) involves determining with a fluorescently labeled polymerase. According to another generally preferred embodiment, when the amplification product includes a universal priming sequence and a sequence complementary to the first barcode; and when sequencing the first barcode in step (d) includes hybridizing a universal primer to the universal priming sequence of the amplification product, and then determining the sequence of the amplification product downstream of the universal primer; the universal primer can be a gated sequencing primer that can be selectively activated. Preferably, the gated sequencing primer includes a blocking group, and the blocking group is removed before extension of the sequencing primer. More preferably, the circular molecule includes a non-natural nucleotide, and the gated sequencing primer is extended by first incorporating a nucleotide that is complementary to the non-natural nucleotide. According to another generally preferred embodiment, the upstream capture nucleic acid sequence and the downstream capture nucleic acid sequence of the capture pair are contiguous with each other. According to another generally preferred embodiment, the first barcode is a single nucleotide. According to another generally preferred embodiment, the circular molecule is produced by connecting the 5'-end of the upstream capture sequence with the 3'-end of the downstream capture sequence, and by connecting the 3'-end of the upstream capture sequence with the 5'-end of the downstream capture sequence. For example, connecting the 5'-end of the upstream capture sequence with the 3'-end of the downstream capture sequence, and connecting the 3'-end of the upstream capture sequence with the 5'-end of the downstream capture sequence can involve performing a ligation reaction. According to another generally preferred embodiment, connecting the 5'-end of the upstream capture sequence with the 3'-end of the downstream capture sequence can involve ligating the two ends to each other. According to another generally preferred embodiment, connecting the 5'-end of the upstream capture sequence with the 3'-end of the downstream capture sequence involves performing nucleic acid extension and ligation reactions. According to another generally preferred embodiment, the first barcode is 1-15 nucleotides in length, the circular molecule includes a universal priming sequence, and the universal priming sequence and the first barcode sequence are separated by 0-10 nucleotides. According to another generally preferred embodiment, the target sequence is a target sequence on chromosome 13, 21, X, Y, or 18. When this is the case, there can be the further step of determining the ploidy status of chromosome 13, 21, X, Y, or 18. According to another generally preferred embodiment, step (c) involves determining the identity of a next correct nucleotide of the first barcode without incorporation of the next correct nucleotide.

In another aspect, the disclosure relates to a method for quantifying a target nucleic acid sequence. The method includes the step of (a) contacting a sample with a capture pair that includes an upstream capture nucleic acid sequence and a downstream capture nucleic acid sequence, where the upstream capture sequence hybridizes to the target sequence upstream relative to the downstream capture sequence, and where the 5'-end of the upstream capture sequence and the 3'-end of the downstream capture sequence are separated by a nick or gap. There also is the step of (b) producing a circular nucleic acid molecule by connecting the 5'-end of the upstream capture sequence and the 3'-end of the downstream capture sequence, where the circular molecule includes a barcode. Further, there is the step of (c) sequencing the barcode. By this sequence determination, an amount or quantity of the target sequence in the sample can be established. According to one generally preferred embodiment, the circular molecule is amplified prior to the step of sequencing the barcode. According to a different preferred embodiment, the upstream capture nucleic acid sequence and the downstream capture nucleic acid sequence of the capture pair can be one contiguous nucleic acid sequence. According to a different preferred embodiment, the circular molecule is produced by connecting the 5'-end of the upstream capture sequence and the 3'-end of the downstream capture sequence, and connecting the 3'-end of the upstream capture sequence and the 5'-end of the downstream capture sequence. For example, connecting the 5'-end of the upstream capture sequence and the 3'-end of the downstream capture sequence, and/or connecting the 3'-end of the upstream capture sequence and the 5'-end of the downstream capture sequence, can be carried out by ligation or extension. According to a different preferred embodiment, connecting the 5'-end of the upstream capture sequence with the 3'-end of the downstream capture sequence can be carried out by ligation. According to a different preferred embodiment, connecting the 5'-end of the upstream capture sequence with the 3'-end of the downstream capture sequence can be carried out by extension and ligation. According to a different preferred embodiment, the gap includes at least 10 nucleotides. According to a different preferred embodiment, the circular molecule includes a universal priming sequence. For example, the universal priming sequence can be located 5' to the barcode sequence. Alternatively, the universal priming sequence and the barcode sequence are separated by a gap of at least 10 nucleotides. Alternatively, sequencing the barcode may involve hybridizing the circular molecule, or the complement thereof, to a sequencing primer and then extending the sequencing primer to determining the sequence of the barcode. Alternatively, when the universal priming sequence and the barcode sequence are separated by a gap of at least 10 nucleotides, the sequencing primer may be a gated sequencing primer that can be selectively activated. When this is the case, the gated sequencing primer can include a blocking group, and the blocking group can be removed before extension of the sequencing primer. Alternatively, the circular molecule includes a non-natural nucleotide, and the gated sequencing primer is extended by first incorporating a nucleotide that is complementary to the non-natural nucleotide. According to a different preferred embodiment, the barcode includes at least 6 nucleotides. For example, the barcode can be only a single nucleotide. According to a different preferred embodiment, the upstream and/or downstream capture sequences of the capture pair can include at least 15 nucleotides. According to a different preferred embodiment, the sample is a blood sample. For example, the sample can be obtained from a pregnant female, and can include both maternal nucleic acids and fetal nucleic acids. According to a different preferred embodiment, the sample is obtained from the pregnant female between 4 and 12 weeks gestation. In certain instances, where the circular molecule is amplified prior to the step of sequencing the barcode, the circular nucleic acid molecule can be amplified by rolling circle amplification. For example, the rolling circle amplification can be performed using phi29 DNA polymerase. Alternatively, the rolling circle amplification can be performed using a barcode sequencing primer, where the nucleotide sequence of the barcode sequencing primer consists of a sequence contained within the capture pair. According to a different preferred embodiment, the sample is obtained from a human. In such an instance, the universal sequencing primers can include non-human sequence of at least 15 nucleotides. According to a different preferred embodiment, the target sequence is a target sequence found on chromosome 13, 21, X, Y, or 18. When this is the case, the method can further include the step of determining that the ploidy status of chromosome 13, 21, X, Y, or 18 is aneuploidy when the number of reads of the target sequence is greater than a control. The control may be a second target nucleic acid sequence that was amplified in the same amplification reaction that amplified the target nucleic acid sequence that is to be quantified.

In another aspect, the disclosure relates to a report displaying a determined ploidy status of a chromosome 13, 21, X, Y, or 18 in a gestating fetus, where the ploidy status was generated using the disclosed method. According to a different preferred embodiment, the method further includes linearly amplifying the capture pair, for example in a rolling circle amplification reaction.

In yet another aspect, the disclosure relates to a method of identifying a nucleic acid sequence variant and the amount of a target sequence in a nucleic acid sample. The method includes the step of (a) contacting a sample with a capture pair including an upstream capture nucleic acid sequence and a downstream capture nucleic acid sequence, where the capture pair is capable of binding to a target nucleic acid sequence surrounding the sequence variant in the sample. Here, the capture pair hybridizes to the target sequence, where the 5'-end of the upstream capture sequence and the 3'-end of the downstream capture sequence are separated by a nick or gap. There also is the step of (b) producing a circular molecule by connecting the 5'-end of the upstream capture sequence and the 3'-end of the downstream capture sequence, where the circular molecular includes a barcode. There also is the step of (c) sequencing the sequence variant to identify the sequence variant. Further, there is the step of (d) sequencing the barcode. By this sequence determination, an amount or quantity of the target sequence in the sample can be established. According to one generally preferred embodiment, the circular molecule is amplified prior to sequence the sequence variant. According to a different preferred embodiment, the circular molecule further includes a universal priming sequence. According to a different preferred embodiment, the circular molecule further includes a variant-specific primer sequence. According to a different preferred embodiment, the gap includes at least 10 nucleotides. According to a different preferred embodiment, the sequence variant is a SNP. When the circular molecule further includes the variant-specific primer sequence, sequencing of the sequence variant can be carried out by extending a variant sequencing primer that is hybridized to the variant-specific primer sequence. In embodiments wherein the circular molecule further includes a universal priming sequence, sequencing of the barcode can be carried out by extending a barcode sequencing primer that is hybridized to the universal priming sequence. For example, the barcode sequencing primer can be a gated primer that can be selectively activated. In other embodiments, when the circular molecule further includes the variant-specific primer sequence, and when sequencing of the sequence variant can be carried out by extending a variant sequencing primer that is hybridized to the variant-specific primer sequence, the variant sequencing primer can be a gated primer that can be selectively activated. Preferably, the gated primer includes a blocking group, and the blocking group is removed before extension of the universal primer. Preferably, the circular molecule includes a non-natural nucleotide, and the gated primer is extended by first incorporating a nucleotide that is complementary to the non-natural nucleotide. In embodiments wherein the circular molecule further includes a universal priming sequence, the universal priming sequence and the barcode sequence can be separated by a gap of at least 10 nucleotides, where the universal primer sequence and the barcode sequence are separated by 0, 1, 2, 3, 4, 5, 6, 7, 8, 9, 10, or more nucleotides. According to a different preferred embodiment, the upstream capture sequence and the downstream capture sequence are included within one contiguous nucleic acid sequence. According to a different preferred embodiment, the upstream capture sequence and the downstream capture sequence are not included within one contiguous nucleic acid sequence. Here, the circular DNA molecule can be produced by connecting the 5'-end of the upstream capture sequence and the 3'-end of the downstream capture sequence, and connecting the 3'-end of the upstream capture sequence and 5'-end of the downstream capture sequence. When this is the case, connecting the 5'-end of the upstream capture sequence with the 3'-end of the downstream capture sequence, and/or connecting the 3'-end of the upstream capture sequence with the 5'-end of the downstream capture sequence can be carried out by ligation or extension. According to a different preferred embodiment, connecting the 5'-end of the upstream capture sequence with the 3'-end of the downstream capture sequence is carried out by ligation. According to a different preferred embodiment, connecting the 5'-end of the upstream capture sequence with the 3'-end of the downstream capture sequence is carried out by extension and ligation. According to a different preferred embodiment, the method further includes linearly amplifying the capture pair. For example, the capture pair can be produced by (i) contacting a first primer including one member of a capture pair with a target sequence, (ii) extending the first primer to form a first extension product, (iii) contacting the first extension product with a second primer including the second member of the capture pair, (iv) extending the second primer to produce a second extension product including both members of the capture pair, and (v) repeating steps (i)-(iv) to linearly amplify the capture pair.

In still another aspect, the disclosure relates to a method of amplifying a target sequence in a sample. This method includes the step of (a) providing a single-stranded circular probe including a sequence complementary to the target sequence. There also is the step of (b) contacting the sample with the single-stranded circular probe to form a hybridized product including the target sequence and the single-stranded circular probe, where forming the hybridized product produces a double stranded portion and at least one single stranded portion in the target sequence. There also is the step of (c) contacting the hybridized product with an enzyme having exonuclease activity, where the enzyme digests the at least one single-stranded portion in target sequence. Further, there is the step of (d) amplifying the circular probe by rolling circle amplification using the digested target sequence as a primer.

In still yet another aspect, the disclosure relates to a method of amplifying a target sequence in a sample. The method includes the step of (a) providing a single-stranded circular probe including a sequence complementary to the target sequence. There also is the step of (b) hybridizing a blocked primer to the circular probe to form a partially double-stranded circular probe, where the partially double-stranded circular probe includes the sequence complementary to the target sequence in the single-stranded region of the circular probe and a recognition site that can be recognized by an endonuclease. There also is the step of (c) contacting the sample with the partially double-stranded circular probe under conditions to form a hybridized product between the target sequence and the partially double-stranded circular probe. There also is the step of (d) contacting hybridized product with the endonuclease, where the endonuclease cleaves the target sequence. Further, there is the step of (e) amplifying the circular probe by rolling circle amplification using the cleaved target DNA sequence as a primer. According to a preferred embodiment, the endonuclease is a nicking endonuclease that recognizes double stranded DNA. The single-stranded circular probe can further include a barcode sequence. When this is the case, the method can further include sequencing the barcode, thereby determining the amount of the target sequence in the sample. Generally speaking, the circular nucleic acid molecule can be detached from the target nucleic acid sequence, and step (a) and (b) can be reiterated to produce additional circular nucleic acid molecules for sequencing.

BRIEF DESCRIPTION OF THE DRAWINGS

FIG. 10A is a schematic showing sequencing of the SNP using a SNP sequencing primer P4901. FIG. 10B is a schematic showing the run off extension of the SNP sequencing primer to the end of the target sequence to prevent interference of sequencing of the barcode sequence (Z4901) shown in FIG. 10A.

FIG. 11A is a schematic showing removal of the 3' blocking group or 3' gate from the barcode sequencing primer. FIG. 11B is a schematic showing sequencing of the barcode (Z4901) using the unblocked barcode sequencing primer. Polymerase is indicated by an open circle in both of FIGS. 11A and 11B.

In FIG. 21A, a second primer is included including a target specific sequence and a sequence complementary to at least a portion of a guide sequence used to direct ligation of the capture pair. In FIG. 21B, a second primer is included that is specific for an additional target sequence variant or SNP so that the resulting capture pair includes two sequence variants.

DETAILED DESCRIPTION

Figure 5:
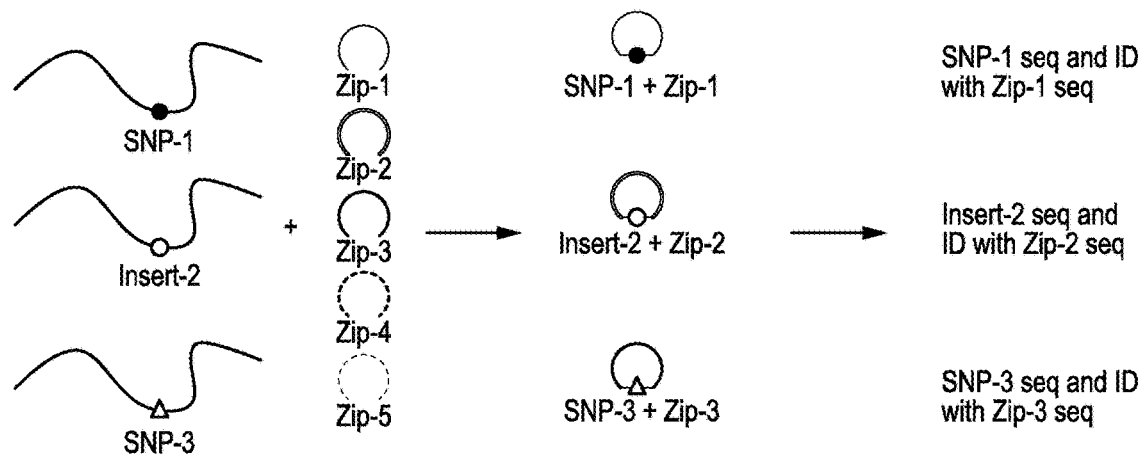
FIG. 5 is a schematic showing the generation of circularized nucleic acid molecules including different sequence variants and barcodes. "SNP-1", "Insert-2", and "SNP-3" represent different sequence variants and "Zip-1"-"Zip-5" represent different barcodes.

Provided herein are methods useful for identifying target sequences, including target sequences containing sequence variants (e.g., SNPs). Target sequences can be identified by sequencing a Zip barcode segment of a synthetic nucleic acid molecule that becomes specifically associated with the target sequence or sequence variant during library construction. The methods are useful for identifying a short sequence variant in a genomic sequence (such as an oncology marker or other genetic determinant) or pathogen sequence (such as a sequence indicative of a particular bacterial or viral species, or drug resistance marker), without having to sequence a large segment of target nucleic acid which would normally be required to determine the sequence context, and thus the identity and relevance of the variant itself. Many sequence variants can be processed simultaneously in a single reaction. For example, FIG. 5 illustrates one embodiment of a multiplex analysis.

Definitions

Practice of the present methods may employ techniques that will be familiar to those having an ordinary level of skill in the fields of organic chemistry, molecular biology, cell biology, and biochemistry (including oligonucleotide synthesis), hybridization, denaturation reaction, amplification reaction, extension reaction, detection of hybridization using a label, and sequencing. Such general methods and techniques can be found in standard laboratory manuals such as *Genome Analysis: A Laboratory Manual Series (Vols. I-IV)*. New York: Cold Spring Harbor Press, 1989; Dieffenbach, C W and Dveksler, G S. *PCR Primer: A Laboratory Manual*. New York: Cold Spring Harbor Press, 2003; Lehninger, *Principles of Biochemistry* 6th Ed., New York: W.H. Freeman, 2012; Berg et al. *Biochemistry*, 5th Ed., New York: W. H. Freeman, 2002; Sambrook, *Molecular Cloning: A Laboratory Manual*. New York: Cold Spring Harbor Press, 1989; Ausubel et al., eds., *Current Protocols in Molecular Biology*. New York: John Wiley & Sons, 1994, and Mount, *Bioinformatics: Sequence and Genome Analysis* $2^{nd}$ Ed., New York: Cold Spring Harbor Press, 2004, all of which are herein incorporated in their entirety by reference for all purposes.

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "DNA" refers to deoxyribonucleic acid in its various forms as understood in the art, such as genomic DNA, cDNA, isolated nucleic acid molecules, vector DNA, and chromosomal DNA. "Nucleic acid" refers to DNA, RNA or analogs thereof in any form. Examples of isolated nucleic acid molecules include, but are not limited to, mRNA, siRNA, miRNA, shRNA, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences that naturally flank the nucleic acid (i.e., sequences located at the 5' and 3'-ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or free of chemical precursors or other chemicals when chemically synthesized.

The term "nucleic acid sequence" or "nucleotide sequence" refers to a nucleic acid material itself and is not restricted to the sequence information (i.e., the succession of letters chosen among the five base letters A, C, G, T, or U) that biochemically characterizes a specific nucleic acid, for example, a DNA or RNA molecule. Nucleic acids shown herein are presented in a 5'-3' orientation unless otherwise indicated.

The terms "polynucleotide," "oligonucleotide" and "nucleic acid" are used interchangeably herein and refer to single-stranded and double-stranded polymers of nucleotide monomers, including without limitation 2'-deoxyribonucleotides (DNA) and ribonucleotides (RNA) linked by internucleotide phosphodiester bond linkages, or internucleotide analogs. A polynucleotide may be composed entirely of deoxyribonucleotides, entirely of ribonucleotides, or chimeric mixtures thereof and can include nucleotide analogs. The nucleotide monomer units may include any nucleotide or nucleotide analog. Unless denoted otherwise, whenever a polynucleotide sequence is represented, it will be understood that the nucleotides are in 5' to 3' order from left to right and that "A" denotes adenosine, deoxyadenosine or an adenine base type, "C" denotes cytidine, deoxycytosine or a cytosine base type, "G" denotes guanosine, deoxyguanosine or a guanine base type, "T" denotes thymidine or a thymine base type, and "U" denotes uridine, deoxyuridine or a uracil base type, unless otherwise noted. The letters A, C, G, and T can be used to refer to the bases themselves, to nucleosides, or to nucleotides including the bases, as is standard in the art. In naturally-occurring polynucleotides, the internucleoside linkage is typically a phosphodiester bond, and the subunits are referred to as nucleotides.

The term "non-natural nucleotide" refers to a nucleotide that is not one of the four standard canonical nucleotides in naturally occurring DNA or RNA. Non-natural nucleotides include, but are not limited to, isoC, isoG, d5SICS, dNaM, dMMO2, 7-(2-thienyl)imidazo[4,5-b]pyridine (Ds), and 4-[3-(6-aminohexanamido)-1-propynyl]-2-nitropyrrole (Px).

The term "polymerase chain reaction" or "PCR" refers to an amplification of a nucleic acid (nucleotide sequence) consisting of an initial denaturation step which separates the strands of a double-stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, *The Polymerase Chain Reaction*, Boston: BirkHauser, 1994). Each of the above steps may be conducted at a different temperature, preferably using an automated thermocycler or similar device. If desired, RNA samples can be converted to DNA/RNA heteroduplexes or to duplex cDNA by methods known to one of skill in the art. The PCR method also includes reverse transcriptase-PCR and other reactions that follow principles of PCR.

The term "primer" refers to a polynucleotide (oligonucleotide) and analogs thereof that are capable of selectively annealing or hybridizing to a target nucleic acid including but not limited to a sequence variant, SNP, a mutation region, or a "template", a target region flanking sequence or to a corresponding primer-binding site of an amplification product. A primer serves as an initiation primer for DNA synthesis under suitable conditions, such as in the presence of appropriate enzyme(s), cofactors, substrates, e.g., nucleotides (dNTPs) and the like. A primer allows the synthesis of a sequence complementary to the corresponding polynucleotide template, flanking sequence or amplification product from the primer's 3'-end. Typically, a primer can be between about 10 to 100 nucleotides in length. Primer sequences can be located within a larger nucleic acid molecule (e.g., a capture pair). The larger nucleic acid molecule containing the primer can also contain other sequences (e.g., barcodes, or restriction sites).

The primers disclosed herein may include adenosine, thymidine, guanosine, and cytidine, as well as uracil, nucleoside analogs (for example, but not limited to, inosine, non-natural nucleotides, locked nucleic acids (LNA), non-nucleotide linkers, peptide nucleic acids (PNA) and phosporamidites) and nucleosides containing or conjugated to chemical moieties such as radionuclides, fluorescent molecules, minor groove binders (MGBs), or any other nucleoside conjugates known in the art.

The term "amplifying" refers to a process whereby a portion of a nucleotide sequence is replicated using, for example, any of a broad range of primer extension reactions. Exemplary primer extension reactions include, but are not limited to, polymerase chain reaction (PCR), multiple displacement amplification (MDA), rolling circle amplification (RCA), nucleic acid sequence-based amplification (NASBA) and bridge amplification. Unless specifically stated, "amplifying" refers to a single replication or to arithmetic, logarithmic, or exponential amplification. Thus, the term "amplification" refers to a method that increases the number of copies of a nucleic acid molecule.

The terms "amplicon," "amplification product," and "amplified sequence" are used interchangeably herein and refer to the product of a broad range of techniques for increasing nucleotide sequences, either linearly or exponentially. An amplicon can be double-stranded or single-stranded, and can include the separated component strands obtained by denaturing a double-stranded amplification product. For example, the amplicon of one amplification cycle can serve as a template in a subsequent amplification cycle. Exemplary amplification techniques include, but are not limited to, PCR or any other method employing a primer extension step. Amplification methods can include thermalcycling or can be performed isothermally. The terms "amplification product" and "amplified sequence" may include products from any number of cycles of amplification reactions.

The term "linear amplification" refers to an amplification of a target, where the number of copies made of the DNA template increases at an approximately linear rate. Linear amplifications are particularly useful in applications like fetal trisomy testing (e.g., non-invasive prenatal testing, or "NIPT"), which require very high precision and very low bias.

The term "extension" refers to the amplification cycle after the oligonucleotide primer and target nucleic acid have annealed to one another, wherein the polymerase enzyme catalyzes primer extension, thereby enabling amplification, using the target nucleic acid as a replication template. The term can also refer to addition of a nucleotide to a primer in a process that does not necessarily result in amplification.

The term "feature" refers to a point, area or volume of a material (e.g., a patterned or random array) that can be distinguished from other points or areas according to relative location. An individual feature can include one or more molecules of a particular type. For example, a feature can include a single target nucleic acid molecule having a particular sequence, or a feature can include an ensemble of several nucleic acid molecules having the same sequence and/or complementary sequence thereof. Different molecules that are at different features of a pattern can be distinguished from each other according to the locations of the features in the pattern. Exemplary features include without limitation, wells in a substrate, beads (or other particles) in or on a substrate, projections (e.g., in situ generated nucleic acid amplification products) from a substrate, pads of gel material on a substrate, or channels in a substrate. Picospheres immobilized to a solid support in a spaced-apart configuration are examples of "nucleic acid features."

The term "sample" refers to a sample suspected of containing a nucleic acid and can include a cell, chromosomes isolated from a cell (e.g., a spread of metaphase chromosomes), genomic DNA, RNA, cDNA and the like. Samples can be of human, non-human, animal, vertebrate, mammalian, fish, invertebrate, plant, prokaryotic, eukaryotic, microbial, viral, or synthetic origins encompassing any organism containing nucleic acid, including, but not limited to, cloned, synthetic constructs, bacteria, viruses, microbes, plants, livestock, household pets, and human samples. Accordingly, the term "nucleic acid sample" may refer to nucleic acid found in biological sources including, but not limited to, for example, hair; stool; blood; plasma; serum; tissue; urine; saliva; cheek cells; vaginal cells; skin for example skin cells contained in fingerprints; bone; tooth; buccal sample; amniotic fluid containing placental cells; amniotic fluid containing fetal cells; and semen. It is contemplated that samples may be collected invasively or noninvasively. In addition to originating from a biological source, a nucleic acid sample can be on, in, within, from or found in conjunction with for example, but not limited to: a fiber, fabric, cigarette, chewing gum, adhesive material, soil, inanimate objects and other forensic samples.

Figure 1:
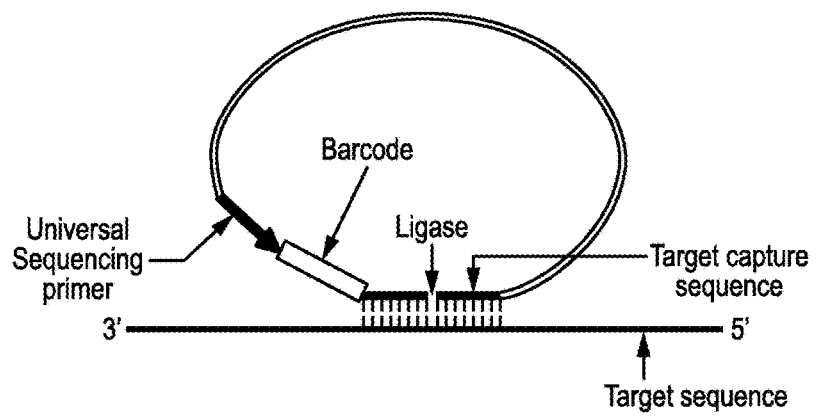
FIG. 1 is a schematic showing a capture pair including a target capture sequence (i.e., upstream and downstream target capture nucleic acid sequences) hybridized to a target sequence. The capture pair also includes the sequence of a universal sequencing primer and a barcode. Upon hybridizing to the target sequence, the capture pair can be ligated to form a circular nucleic acid molecule. "Ligase" indicates the position at which a ligase enzyme acts to join two ends of the capture pair. Upstream and downstream capture nucleic acid sequences (i.e., sequences that hybridize to complementary regions within the target sequence) are shown as being contiguous, or contained within the same nucleic acid molecule.
Figure 2:
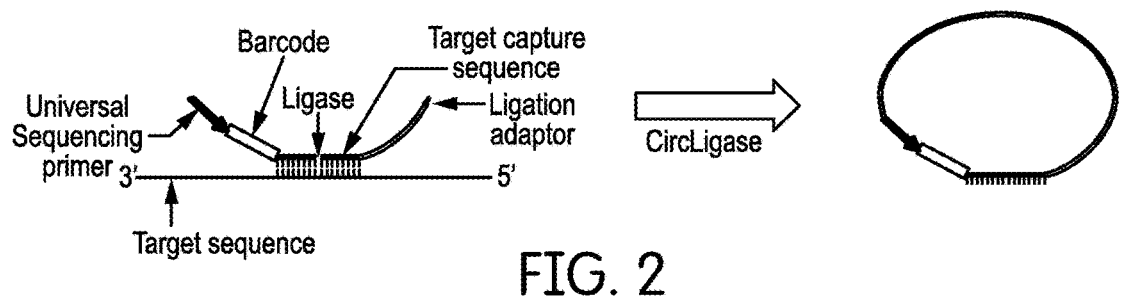
FIG. 2 is a schematic showing a capture pair including a target capture sequence hybridized to a target sequence. The capture pair also includes the sequences of a universal sequencing primer and a barcode. Upon hybridizing to the target sequence, the capture pair can be ligated to form a linear nucleic acid. CircLigase can then be used to ligate the ends of the capture pair to form a circular nucleic acid molecule. Upstream and downstream capture nucleic acid sequences (i.e., sequences that hybridize to complementary regions within the target sequence) are shown as being present on different nucleic acid molecules.
Figure 3:
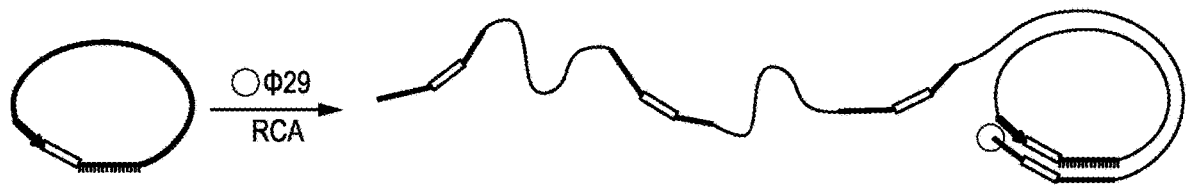
FIG. 3 is a schematic showing amplification of a circular nucleic acid molecule by rolling circle amplification (RCA) to form a picosphere. The RCA is mediated by the phi29 DNA polymerase, which is shown as an open circle.
Figure 4:
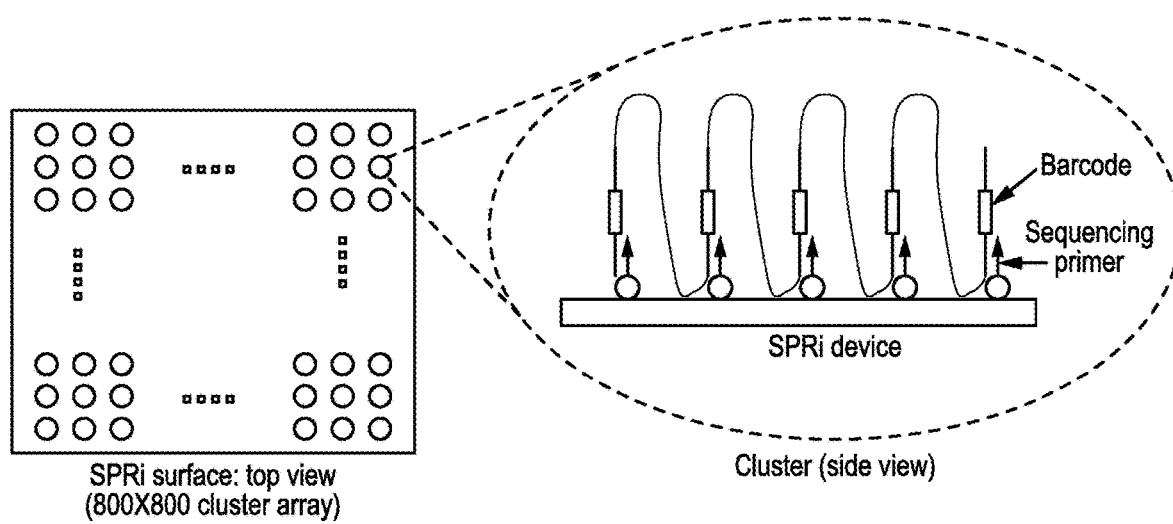
FIG. 4 is a schematic showing the picosphere bound to a sequencing primer on a surface. The sequencing primer (or barcode sequencing primer) is adjacent to the barcode sequence, so that the primer extends first into the barcode sequence (or the complement thereof), and thereafter into the connected target capture sequences (or the complement thereof).

The term "capture pair" refers to two nucleic acid sequences that hybridize to different regions of a nucleic acid target sequence. The capture pair hybridizes to the target sequence in such a manner that a portion of the capture pair hybridizes to a region upstream of a second portion of the capture pair and is referred to as the "upstream capture nucleic acid sequence." The second portion of the capture pair is referred to as the "downstream capture nucleic acid sequence." This arrangement is illustrated, for example, FIGS. 1 and 2. Arrows in each figure that indicate "Target capture sequence" are directed to the upstream capture nucleic acid sequences. Each sequence of the capture pair can be any nucleic acid sequence, possibly modified, that is generated by various methods, such as PCR or direct synthesis, and are intended to be complementary to one strand of a specific DNA target sequence in a sample. The upstream and downstream capture nucleic acid sequences can be on the same nucleic acid molecules (i.e., contiguous sequences, as shown in FIG. 1), or on different nucleic acid molecules (as shown in FIG. 2).

Optionally, the term "capture pair" refers to the single stranded nucleotide that is hybridized to the target sequence in a sample nucleic acid, and that has ends that can be joined to form a circularized nucleic acid molecule that includes the complement of the target sequence. This is illustrated in FIG. 1.

The term "circular nucleic acid molecule" (or "circle," when used in reference to a nucleic acid) refers to a circular nucleic acid molecule including a target sequence (e.g., a SNP). Optionally, the circular nucleic acid molecule (or "circle") includes one or more sequences selected from the group consisting of a universal priming sequence, a barcode sequence, and a variant-specific primer sequence.

The term "guide sequence" refers to a nucleic acid sequence that is capable of binding to a linear nucleic acid sequence (e.g., a capture pair), to facilitate ligation of the linear nucleic acid sequence to form a circular molecule. As disclosed herein, the guide sequence may align the ends of a linear nucleic acid sequence to facilitate ligation of the 5' and 3'-ends of the linear nucleic acid sequence. Optionally, the guide sequence binds two non-contiguous nucleic acids and facilitates ligations of the nucleic acids to form a linear molecule.

The term "nick" refers to the absence of a phosphodiester bond between a terminal nucleotide from a first single polynucleotide strand and a terminal nucleotide from a second polynucleotide strand hybridized to adjacent sequences in a third single polynucleotide strand. For example, the 5'-end of the upstream capture sequence and the 3'-end of the downstream capture sequence are separated by a nick when they hybridize to adjacent nucleotides in the target sequence and can be ligated together by a ligase.

The term "gap," when used in reference to a double stranded nucleic acid, refers to a break in the covalent connectivity of the sugar phosphate backbone of a nucleic acid strand that causes absence of one or more nucleotides within the strand. Due to the absence of nucleotide(s), a gap is further characterized by the upstream 3' hydroxyl of the strand not being adjacent to the downstream 5' phosphate of the strand.

For the purpose of this disclosure, the terms "barcode" and "Zip barcode" are interchangeable and refer to a sequence used to identify a target sequence to which it is associated. In general, barcodes are designed to be easily sequenced at high accuracy, with low probability of errors for the sequencing technology being used. Barcodes can also be designed merely for convenience. As an example, the barcode sequences can be selected to avoid or omit homopolymer stretches, thereby simplifying the sequence determination procedure. Additionally, features can be engineered such that one or several possible sequencing errors can be detected and corrected. As an example of the latter, merely repeating a short barcode 3 times (e.g. GTCAGTCAGTCA (SEQ ID NO:4)) will enable correcting multiple individual read errors simply by consensus.

Optionally, the term "barcode" or "Zip barcode" refers to a single nucleotide or multiple nucleotides used to identify one or more target sequences. Thus, barcodes may include 1-30 nucleotides in length or any number of nucleotides between 1 and 30, inclusive. Optionally, the barcode is from 6-20 nucleotides in length. Optionally, the barcode is 1, 2, 3, 4, 5, 6, 7, 8, 9, 10, 11, 12, 13, 14, 15, or more nucleotides in length.

The term "sequence variant" refers to one of the variations in a position or region of the genome among the members of the same species or the complement thereof. Non-limiting examples of sequence variants include allele variants of a gene, and SNPs. A sequence variant can also be a prognostic or diagnostic marker for a disease, such as cancer.

The term "Single Nucleotide Polymorphism (SNP)" refers to a sequence variation occurring commonly within a population in which a single nucleotide—A, T, C, or G—in the genome differs between members of a biological species or paired chromosomes.

As used herein, the term "universal priming sequence" means a region of nucleotide sequence that is common to two or more nucleic acid molecules (e.g., different circularized templates, or different rolling circle amplification products), where the two or more nucleic acid molecules also have regions of sequence differences (e.g., different barcodes). A universal priming sequence that may be present in different members of a collection of nucleic acid molecules can allow the replication or amplification of multiple different sequences using a universal primer that is complementary to the universal priming sequence. Thus, "universal primers" are nucleic acid molecules having a common nucleotide sequence that hybridizes specifically to the same universal priming sequence. It will be understood that the common nucleotide sequence in a population of universal primers can be all or a portion of the primers so long as the nucleotide sequence is of sufficient length to hybridize specifically under the conditions used. An exemplary universal priming sequence is a DNA sequence that may be appended to a population of target DNA molecules, for example, by ligation, PCR, or ligation mediated PCR. Once added to the population of target molecules, primers specific to the universal priming sequences can be used to detect, amplify and/or sequence the target sequences. Optionally, the universal priming sequence is adjacent to a barcode sequence, and a primer that can hybridize specifically to the universal priming sequence (i.e., a barcode sequencing primer), is used to sequence the barcode, thereby detecting the target sequence. The arrangement of the universal priming sequence, the barcode complement, and the target capture sequence complement in an amplification product (e.g., an RCA product) is such that the barcode sequencing primer must first extend through the barcode region (i.e., using the barcode complement as template) before extending into the connected target capture sequences (i.e., using the target capture complement as template). Optionally, the universal priming sequence is also used to amplify a nucleic acid molecule (e.g., a circularized capture pair using amplification primers). Optionally, a capture pair or circularized capture pair includes two universal priming sequences. The first universal priming sequence can contain a sequence complementary to a barcode sequencing primer, and the second universal priming sequence can contain a sequence complementary to an amplification primer. Universal priming sequences are typically not related to (e.g., not contained within) the target sequences.

The term "variant sequencing primer" refers to a primer that can hybridize to a sequence adjacent to the variant (e.g., SNP), on a nucleic acid molecule and extension of the primer can produce sequence information about the sequence variant. When the sequence variant is a SNP, the corresponding variant sequencing primer can be referred to as the SNP sequencing primer.

The term "barcode sequencing primer" refers to a primer that can hybridize to a nucleic acid molecule including a universal priming sequence and a barcode and extension of the primer can produce sequence information about the barcode. Optionally, the barcode sequencing primer is attached to a suitable surface. The barcode sequencing primer is also referred to herein as a Zip barcode primer. A barcode sequencing primer can be a universal primer that is complementary to a universal priming sequence.

The term "gated primer" refers to a primer that is prevented from extension by a blocking mechanism (i.e., a gate, until the gate is opened or removed), which activates or unblocks the gated primer. Optionally, the gate is a blocking group.

The term "blocking group" or "blocking moiety" refers to a part of the nucleotide that inhibits or prevents the nucleotide from forming a covalent linkage to a second nucleotide (e.g., the 3' position of a primer nucleotide can be attached to a blocking group) during the incorporation step of a nucleic acid polymerization reaction. The blocking group can be modified or removed from the nucleotide, allowing for nucleotide incorporation during primer extension. For example, the blocking group of a "reversible terminator" nucleotide can be removed from the nucleotide analog to allow for nucleotide incorporation. Such a blocking moiety is referred to herein as a "reversible terminator moiety." Exemplary reversible terminator moieties are set forth in U.S. Pat. Nos. 7,427,673; 7,414,116; and 7,057,026 and PCT publications WO 91/06678 and WO 07/123744, each of which is incorporated by reference.

The term "chromosome" may refer to a single chromosome copy, meaning a single molecule of DNA of which there are 46 in a normal human somatic cell (e.g. "the maternally derived chromosome 18"). Chromosome may also refer to a chromosome type, of which there are 23 in a normal human somatic cell (e.g., "chromosome 18").

The term "ploidy status" refers to the quantity and/or chromosomal identity of one or more chromosome types in a cell.

The term "aneuploidy" refers to an abnormal number of chromosomes in a cell. Most cells in the human body have 23 pairs of chromosomes, or a total of 46 chromosomes. The most common aneuploidy in human population is trisomy 21 (three copies of chromosome 21), which is found in Down syndrome, affecting 1 in 800 births; trisomy 18 (Edwards syndrome) affecting 1 in 6000 births, and trisomy 13 (Patau syndrome) affecting 1 in 10,000 births.

The term "exonuclease" refers to enzymes that can cleave nucleotides by breaking phosphodiester bonds one at a time from the end (exo) of a polynucleotide chain. A 5'-3' exonuclease removes nucleotide in the 5' to 3' direction and a 3'-5' exonuclease removes nucleotide in the 3'-5' direction.

The term "endonuclease" refers to enzymes that can cleave nucleotides by breaking phosphodiester bonds in the middle (endo) of a polynucleotide chain. Nicking endonucleases are endonucleases that recognize specific sites in the double-stranded DNA, but hydrolyzes only one strand of the duplex, to produce DNA molecules that are "nicked", rather than cleaved. These conventional nicks (3'-hydroxyl, 5'-phosphate) can serve as initiation points for a variety of further enzymatic reactions such as replacement DNA synthesis and strand-displacement amplification.

The term "number of reads" refers to the number of times a particular nucleotide or series of nucleotides is read during a sequencing reaction.

Throughout the disclosure DNA targets are explicitly mentioned, but RNA targets may also be used with suitable or no modification to the procedure as described. Additionally, identification by sequencing, especially for Zip barcodes, is explicitly mentioned, but other identification methods can also be used, such as specific hybridization to a labeled probe, hybridization to a known location on an ordered array, and the like.

Targets or target sequences can be any sequences and can be derived from either human or non-human species. Optionally, a target sequence is a sequence derived from a human subject and the presence or absence of which correlates with a disease status. Optionally, the target sequence is a DNA region surrounding a sequence variant (e.g., a SNP). Optionally, the target sequence is a sequence on a chromosome (e.g., chromosome 13, 18, or 21). Quantitation of a target sequence specific to one of these chromosomes relative to a control can reveal the ploidy status of the chromosome, which correlates with a diagnosis whether the subject has certain genetic diseases. For example, a trisomy of chromosome 21, which can be detected by quantifying a target sequence on chromosome 21, provides a diagnosis of Down Syndrome; while a trisomy of Chromosome 18 provides a diagnosis of Edward's Syndrome. It is rare in human population to have aneuploidy in chromosome 1, thus sequences specifically present in chromosome 1 can be used as an internal control. Optionally, one or more chromosomes or other sequences can serve as control sequences.

A "control" or "standard control" refers to a sample, measurement, or value that serves as a reference, usually a known reference, for comparison to a test sample, measurement, or value. For example, a test sample can be taken from a patient suspected of having a given disease or disorder (e.g., trisomy, an autoimmune disease, inflammatory autoimmune disease, cancer, infectious disease, immune disease, or other disease) and compared to a known normal (non-affected) individual (e.g. a standard control subject). A standard control can also represent an average measurement or value gathered from a population of similar individuals (e.g. standard control subjects) that do not have a given disease or disorder (i.e. standard control population). These may be healthy individuals with a similar medical background, same age, weight, and the like. A standard control value can also be obtained from the same individual (e.g. from an earlier-obtained sample from the patient prior to disease onset). In yet another aspect, a control (e.g., a normalization control) can be a detected and quantified amplification product, where the amplification product was produced using a capture pair that circularized in a manner dependent on a second target sequence being present in the same sample. For example, a normalization control used in a procedure for assessing trisomy 21 (i.e., a first target sequence being present on chromosome 21) may be represented by a second target sequence that is present on a chromosome other than chromosome 21.

Target sequences can be incorporated into capture pairs as described herein and converted into circular nucleic acid molecules ("circles" or "circle templates") before detection, as described in the sections below. Optionally, the method is used to incorporate different target sequences into capture pairs simultaneously. For example, capture pairs can be engineered to have different barcodes associated with the same or different target sequences in each of the target chromosomes, 13, 18, 21, so that diagnosis of multiple diseases can be made simultaneously. The target sequence disclosed herein refers to the target sequence as may be present in the sample, or the complement thereof (e.g., those produced by methods described herein).

As used herein, a "binary complex" is a complex between a polymerase and a primed template nucleic acid (or blocked primed template nucleic acid), where the complex does not include a nucleotide molecule such as the next correct nucleotide.

As used herein, a "ternary complex" is a complex between a polymerase, a primed template nucleic acid (or blocked primed template nucleic acid), and the next correct nucleotide positioned immediately downstream of the primer and complementary to the template strand of the primed template nucleic acid or the blocked primed template nucleic acid. The primed template nucleic acid can include, for example, a primer with a free 3'-OH or a blocked primer (e.g., a primer with a chemical modification on the base or the sugar moiety of the 3' terminal nucleotide, where the modification precludes enzymatic phosphodiester bond formation).

As used herein, "FRET" (i.e., fluorescence resonance energy transfer) refers to the distance-dependent radiationless transmission of energy quanta from the site of absorption to the site of its utilization in a molecule or system of molecules by resonance interaction between chromophores.

As used herein, a "flow cell" is a reaction chamber that includes one or more channels that direct fluid in a predetermined manner to conduct a desired reaction. The flow cell can be coupled to a detector such that a reaction occurring in the reaction chamber can be observed. For example, a flow cell can contain primed template nucleic acid molecules (or blocked primed template nucleic acid molecules), for example, tethered to a solid support, to which nucleotides and ancillary reagents are iteratively applied and washed away. The flow cell can include a transparent material that permits the sample to be imaged after a desired reaction occurs. For example, a flow cell can include a glass slide containing small fluidic channels, through which polymerases, dNTPs and buffers can be pumped. The glass inside the channels can be decorated with one or more primed template nucleic acid molecules to be sequenced. An external imaging system can be positioned to detect the molecules on the surface of the glass. Reagent exchange in a flow cell is accomplished by pumping, drawing, or otherwise "flowing" different liquid reagents through the flow cell. Exemplary flow cells, methods for their manufacture and methods for their use are described in US Pat. App. Publ. Nos. 2010/0111768 A1 or 2012-0270305 A1; or WO 05/065814, each of which is incorporated by reference herein.

As used herein, the phrase "quantifying the amplification product by sequencing the barcode" refers to the process of determining the quantity of an amplified circular template molecule in numerical terms using barcode sequence detection. Here, one nucleic acid feature containing a particular barcode sequence reflects or indicates one circular template molecule was present in an amplification reaction. This quantitation may involve, for example, counting (e.g., in an automated fashion) the number of nucleic acid features having the same barcode within a field of view under a microscope. The phrase embraces quantitative methods based on comparison of numbers of nucleic acid features having different barcode sequences (e.g., where the number of instances of one barcode serves as a control or comparator for a different barcode).

Various aspects of the provided methods include incorporating a target sequence into a capture pair and circularizing the capture pair to produce a circular nucleic acid molecule. In one approach, a nucleic acid sample is contacted with a capture pair, which hybridizes to the target sequence. The capture pair includes an upstream capture nucleic acid sequence and a downstream nucleic acid sequence and when hybridized to the target sequence, the upstream capture nucleic acid sequence and downstream capture nucleic acid sequence are separated by a nick or a gap of 1, 2, 3, 4, 5, 6, 7, 8, 9, 10, or more nucleotides. Optionally, the two segments of the capture pair can be separated by a gap of more than 10 nucleotides on the target sequence. Thus, the two segments of the capture pair can be separated by a gap of 10, 20, 30, 40, 50, 60, 70, 80, 90, 100 or more nucleotides.

In the cases where the region 5' of the upstream nucleic acid sequence and the region 3' of the downstream nucleic acid are paired to the adjacent nucleotides in the target sequence, a nick separates the upstream and downstream capture nucleic acid sequences. A ligase is used to ligate the two ends of the capture nucleic acid sequences to form a continuous nucleic acid strand, closing the nick. Optionally, ligation produces a circular nucleic acid molecule. Ligases suitable for use in the provided methods are known and include, for example, thermophilic ligase, archael ligase, RNA ligase, and enzymes that favor either cohesive or blunt end ligation. Ligases include, for example, T4 DNA ligase (NEB), ligase I, ligase iii, ligase iv, *E. coli* DNA ligase, T4 RNA ligase, Taq DNA ligase, archaeal *Thermococcus* species DNA ligase, strain 9° N DNA ligase, RNA ligase from *M. thermoautotrophicum*, T7 DNA ligase, *Chlorella* virus DNA ligase.

Where the region 5' of the upstream nucleic acid sequence and the region 3' of the downstream capture sequence are paired to non-adjacent nucleotides, the two ends of the capture pair are separated by a gap of N nucleotides. A DNA polymerase is added to extend the 3'-end of the downstream capture nucleic acid sequence by adding bases to complementary to the single stranded region on the target sequences, which fills the gap between the two ends of the capture pair. Afterward, the 3'-end of the extended, downstream capture nucleic acid sequence is ligated to the 5'-end of the upstream capture nucleic acid sequence. DNA polymerases include, but are not limited to, bacterial DNA polymerases, eukaryotic DNA polymerases, archaeal DNA polymerases, viral DNA polymerases, phage DNA polymerases and reverse transcriptases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases $\alpha$, $\beta$, $\gamma$, $\delta$, $\epsilon$, $\eta$, $\zeta$, $\lambda$, $\sigma$, $\mu$, and k, as well as the Rev1 polymerase (terminal deoxycytidyl transferase) and terminal deoxynucleotidyl transferase (TdT). Viral DNA polymerases include T4 DNA polymerase, phi29 DNA polymerase, GA-1, phi29-like DNA polymerases, PZA DNA polymerase, phi-15 DNA polymerase, Cp1 DNA polymerase, Cp7 DNA polymerase, T7 DNA polymerase, and T4 polymerase. Archaeal DNA polymerases include thermostable and/or thermophilic DNA polymerases such as DNA polymerases isolated from *Thermus aquaticus* (Taq) DNA polymerase, *Thermus filiformis*

(Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; Desulfurococcus strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Examples of reverse transcriptases include Avian Myelobrastosis Virus (AMV) Reverse Transcriptase, Moloney Murine Leukemia Virus (M-MuLV) Reverse Transcriptase, and Human Immunodeficiency Virus (HIV) Reverse Transcriptase. Also useful are variants of naturally occurring nucleic acid polymerase enzymes engineered to eliminate, decrease, add or enhance particular attributes. Indeed, engineered and modified polymerases also are useful in connection with the disclosed techniques. For example, modified versions of the extremely thermophilic marine archaea *Thermococcus* species 9° N (e.g., Therminator DNA polymerase from New England BioLabs Inc.; Ipswich, Mass.) can be used. Still other useful DNA polymerases, including the 3PDX polymerase are disclosed in U.S. Pat. No. 8,703,461, the disclosure of which is incorporated by reference in its entirety.

Optionally, the upstream capture and downstream capture nucleic acid sequences are contained within one contiguous nucleic acid molecule, with the upstream capture sequence located at one end of the nucleic acid and the downstream capture sequence located at the other end of the nucleic acid. The contiguous capture pair, upon hybridizing to the target, forms an inverted molecule such that the 5'-end of the upstream capture nucleic acid sequence and the 3'-end of the downstream capture nucleic acid sequence are paired with the nucleotides in the target and separated by a nick or gap of 1, 2, 3, 4, 5, 6, 7, 8, 9, 10, 20, 30, 40, 50, 60, 70, 80, 90, 100 or more nucleotides (see FIG. 1). Optionally, the two segments of the capture pair can be separated by a gap of more than 10 nucleotides on the target sequence.

Optionally, the upstream capture nucleic acid sequence and the downstream capture nucleic acid sequence are two separate sequences (i.e., on two different DNA molecules). In addition to joining the 5'-end of the upstream capture nucleic acid sequence and the 3'-end of the downstream capture nucleic acid sequence, a ligase can be used to join the 3' and 5'-ends of the capture pair (see FIG. 2). Ligases suitable for this purpose are those that catalyze intramolecular ligation (i.e., circularization) of ssDNA templates having a 5'-phosphate and a 3'-hydroxyl group, in the absence of a complementary sequence. Non-limiting examples of such ligases include CircLigase (Epicentre; Madison, Wis.).

Optionally, the upstream and downstream capture nucleic acid are hybridized to the target DNA region including or surrounding a sequence variant (e.g., a SNP).

Optionally, a circular nucleic acid molecule is formed by aligning a single stranded nucleic acid including the target sequence on a single-stranded or partially double-stranded guide sequence. The single-stranded portion of the guide sequence hybridizes to the two ends of the nucleic acid including the target sequence. The ends of the single strand target sequence can be ligated with the ends of the double stranded portion of the guide sequence to produce a circle (see FIG. 6).

Optionally, the circular nucleic acid molecules produced by the present method also include a universal priming sequence, a barcode, and/or a variant-specific sequence, which may be originated from the upstream capture nucleic acid sequence or the downstream capture nucleic acid sequence. The universal priming sequence and the barcode in the circular nucleic acid molecules can be adjacent to each other or can be separated by one or more nucleotides (e.g., from 0 to 30 nucleotides, inclusive). Optionally, the universal priming sequence and the barcode are separated by 0, 1, 2, 3, 4, 5, 6, 7, 8, 9, or 10 nucleotides, and a barcode sequencing primer can hybridize to the universal priming sequence and be used directly or extended to produce the sequence information of the barcode. Likewise, the variant-specific primer sequence and the sequence variant can be adjacent to each other or can be separated by one or more nucleotides.

Optionally, the circular nucleic acid molecules are amplified, for example, by "rolling circle" amplification ("RCA"). For RCA, a primer can be hybridized to the circle, then extended continuously with a strand displacing DNA polymerase to create a very long DNA concatemer; or an RNA polymerase can associate with a promoter in the circular construct and transcribe a very long RNA concatemer. The large concatemer contains many copies of the variant SNP and Zip barcode (as described below) which are subsequently identified during the sequencing reaction. Many target templates can be constructed then amplified in a single reaction.

There is flexibility in the method of preparing nucleic acid features containing barcode sequences that are to be detected and quantified (e.g., counted) by the disclosed approach. When circular template molecules are amplified by rolling circle amplification, RCA reactions may be performed in one of two general ways. In either case, a single RCA product containing many copies of the same barcode represents a single nucleic acid feature derived from a single circular template molecule. When mixtures of different types of circular templates are used in a single RCA reaction, there can be produced a collection of picospheres, with each picosphere representing a single starting circular template molecule. Fixing or immobilizing these picospheres to a solid support or surface for subsequent processing permits nucleic acid feature analysis. Simply counting features containing a particular barcode sequence verifies the presence of the relevant target sequence in a test sample, and provides information that can be used for quantifying the target sequence. Optionally, features containing different barcode sequences can be counted, and the instances of each barcode compared for further quantitative insights. This can be useful, for example, in detecting nucleic acid segments diagnostic of disease-causing organisms, chromosomal aneuploidy, etc.

In one embodiment, the RCA reaction can be performed in solution using primers and circular templates that are free in solution, as opposed to having one or the other of those components immobilized to a solid support. Once synthesized, the picosphere amplification products can be deposited onto a solid support to create a field of nucleic acid features. The features optionally may be arranged in a spatially predetermined order. Distinct from an ordered array of nucleic acid features, nucleic acid features in accordance with the procedure may be arranged in a "random" array.

In another embodiment, the RCA reaction is carried out on a surface using at least one immobilized component (e.g., primer, circular template, or polymerase). For example, single-stranded circular DNA templates to be analyzed can be captured by primers immobilized onto an inner surface of a flow cell. This may involve use of biotinylated primers captured onto a streptavidin surface within the flow cell. Alternatively, primers may be covalently joined to the material of the flow cell surface, or a coating or passivation layer thereon. Reagents used for promoting amplification reactions (e.g., enzymes, nucleotides, buffers, cofactors, etc.) can be flowed through the flow cell to synthesize picospheres in situ (i.e., in place). Again, there is no requirement for the resulting nucleic acid features to be arranged in a spatially predetermined order.

Primers that can be used to amplify the circles can be any sequences suitable for the purpose of this disclosure. Optionally, the primer used for the amplification reaction is the barcode sequencing primer, or the variant sequencing primer. Optionally, the primer used for the rolling circle amplification (RCA) reaction is complementary to a portion of the target in the sample nucleic acid itself. Optionally the primer is formed by cleavage, modification or other processing of the target nucleic acid which is hybridized to the binding pair of the circle template. Optionally, the primer is complementary to one or both segments of the binding pair. Optionally, the RCA primer is complementary to a universal priming sequence.

Optionally, the RCA primer is an immobilized primer that captures a circularized nucleic acid template at a universal RCA priming sequence contained therein. Typically, the circularized nucleic acid template includes: a barcode sequence; an upstream sequence corresponding to the sequence of a universal barcode sequencing primer; and a target capture sequence resulting from connection of the upstream and downstream target capture sequences of the target capture pair. Preferably, the immobilized RCA primer captures the circular template by hybridizing to a universal RCA priming sequence that is independent of each of these other sequences. The portion of the circular template that hybridizes to the immobilized primer has sometimes been referred to as "vector" sequence to indicate independence from these other sequences, while indicating the immobilized RCA primer can be common to different circular templates having different barcodes, and different connected target-specific upstream and downstream target capture sequences. Optionally, the immobilized common RCA primer is complementary to a sequence contained within the circular template, where the RCA primer-complementary sequence is spaced apart from barcode sequence, the universal barcode sequencing primer sequence, and the connected target-specific upstream and downstream target capture sequences. For example, these may be spaced-apart by 0-50 nucleotides, 0-25 nucleotides, or any other separation as may be selected by an end-user. By these arrangements, the picosphere synthesized in situ advantageously can be anchored to a solid support at a single attachment point.

Polymerases that can be used for RCA are those having the ability to displace downstream DNA encountered during synthesis by causing the dissociation of a paired nucleic acid from its complementary strand in a direction from 5' towards 3', in conjunction with, and close to, the template-dependent nucleic acid synthesis. The strand displacement starts at the 5' end of a paired nucleic acid sequence and the enzyme therefore carries out the nucleic acid synthesis immediately 5' of the displacement site. The newly synthesized nucleic acid strand and the displaced nucleic acid strand generally have the same nucleotide sequence, which is complementary to the template nucleic acid strand. Non-limiting examples of DNA polymerases suitable for the RCA include phi29 polymerase, large fragment of Bst DNA polymerase, large fragment of Bsu DNA polymerase. Klenow fragment of *E. coli* DNA polymerase I, T5 bacteriophage DNA polymerase, M-MuLV Reverse Transcriptase, HIV virus reverse transcriptase, and Deep-VentR DNA polymerase (NEB #M0258). Additionally, genetically engineered variants of naturally occurring nucleic acid polymerase enzymes may eliminate 5'-3' exonuclease activity, or modify other properties to improve strand displacement activity.

Rolling circle amplification produces a linear concatermic nucleic acid molecule, which takes the form of a random coil, commonly referred to as a "picosphere." A picosphere can be immobilized to a surface suitable for sequencing (e.g., via hybridizing to a universal capture oligonucleotide on the surface of a sequencing substrate). The universal capture oligonucleotide has a sequence that is unrelated to any specific target sequence of interest and thus can be used to capture any target sequences. Optionally, the universal capture oligonucleotide can hybridize to the universal priming sequence in the picospheres. Optionally, the universal capture oligonucleotide is a barcode sequencing primer. Alternatively, the picospheres may be attached to the surface through ionic interactions, via covalent linkages, or mediated through binding of attached ligands (e.g. biotin and streptavidin). Optionally, one or several sequencing primers may be hybridized to the picosphere before or after attachment to the surface for sequencing.

The target sequences and Zip barcodes can be associated into capture pairs that can be amplified by other methods as well. These include exponential methods such as PCR, strand displacement amplification, MDA, isothermal transcription associated amplification (e.g. TMA, NASBA) and so on. Amplification can also be linear, such as cycling primer extension, cycling ligation, continuous transcription by RNA polymerases, or a combination of linear methods (see FIGS. 25-29).

Useful sequencing platforms for use in the provided methods include, but are not limited to, sequencing-by-synthesis (i.e., sequencing-by-incorporation), pH-based sequencing, sequencing by polymerase monitoring, sequencing by hybridization, and other methods of massively parallel sequencing or next-generation sequencing. Optionally, the sequencing is carried out as described in U.S. patent application Ser. No. 14/805,381, which is incorporated by reference herein in its entirety. Suitable surfaces for carrying out sequencing include, but are not limited to, a planar substrate, a hydrogel, a nanohole array, a microparticle, or nanoparticle. Exemplary sequencing platforms including methods, reagents and solid-phase surfaces are set forth below and in the cited references.

Particularly useful sequencing reactions are sequencing-by-binding reactions as described in commonly owned U.S. patent application Ser. No. 14/805,381; 62/447,319; 62/440,624; or 62/450,397, each of which is incorporated by reference. Generally, methods for determining the sequence of a template nucleic acid molecule can be based on formation of a ternary complex (between polymerase, primed nucleic acid and cognate nucleotide) under specified conditions. The method can include an examination phase followed by a nucleotide incorporation phase.

The examination phase in a sequencing-by-binding procedure can be carried out in a flow cell having at least one template nucleic acid molecule (e.g., an RCA product) primed with a primer; contacting the primed template nucleic acid molecule(s) with a first reaction mixture that includes a polymerase and at least one nucleotide type; observing the interaction of polymerase and a nucleotide with the primed template nucleic acid molecule(s), under conditions where the nucleotide is not covalently added to the primer(s); and identifying a next base in each template nucleic acid using the observed interaction of the polymerase and nucleotide with the primed template nucleic acid molecule(s). The interaction between the primed template, polymerase and nucleotide can be detected in a variety of schemes. For example, the nucleotides can contain a detectable label. Each nucleotide can have a distinguishable label with respect to other nucleotides. Alternatively, some or all of the different nucleotide types can have the same label and the nucleotide types can be distinguished based on separate deliveries of different nucleotide types to the flow cell. In some embodiments, the polymerase can be labeled. Polymerases that are associated with different nucleotide types can have unique labels that distinguish the type of nucleotide to which they are associated. Alternatively, polymerases can have similar labels and the different nucleotide types can be distinguished based on separate deliveries of different nucleotide types to the flow cell (e.g., delivering the labeled polymerase in combination with one or more unlabeled nucleotides at a time).

During the examination phase, discrimination between correct and incorrect nucleotides can be facilitated by ternary complex stabilization. A variety of conditions and reagents can be useful. For example, the primer can contain a reversible blocking moiety that prevents covalent attachment of nucleotide, and/or cofactors that are required for extension, such as divalent metal ions can be absent, and/or inhibitory divalent cations that inhibit polymerase-based primer extension can be present, and/or the polymerase that is present in the examination phase can have a chemical modification and/or mutation that inhibits primer extension, and/or the nucleotides can have chemical modifications that inhibit incorporation, such as 5' modifications that remove or alter the native triphosphate moiety.

The extension phase can then be carried out by creating conditions in the flow cell where a nucleotide can be added to the primer on each template nucleic acid molecule. In some embodiments, this involves removal of reagents used in the examination phase and replacing them with reagents that facilitate extension. For example, examination reagents can be replaced with a polymerase and nucleotide(s) that are capable of extension. Alternatively, one or more reagents can be added to the examination phase reaction to create extension conditions. For example, catalytic divalent cations can be added to an examination mixture that was deficient in the cations, and/or polymerase inhibitors can be removed or disabled, and/or extension competent nucleotides can be added, and/or a deblocking reagent can be added to render primer(s) extension competent, and/or extension competent polymerase can be added. Optionally, the nucleotide that is enzymatically incorporated into the primer strand of the primed template nucleic acid molecule is different from the nucleotide used in the examination step to identify the next correct nucleotide. Optionally, the incorporated nucleotide is a reversible terminator nucleotide, where primer extension is limited to a single nucleotide incorporation prior to removal of a reversible terminator moiety. Optionally, the polymerase used in the incorporation step is different from the polymerase used in the examination step. Thus, for embodiments employing reversible terminator nucleotides, a deblocking reagent can be delivered to a flow cell (before or after detection occurs). Washes can be carried out between the various delivery steps. The cycle can then be repeated n times to extend the primer by n nucleotides (e.g., by incorporating only reversible terminator nucleotides), thereby detecting a sequence of length N.

The above examination and extension phases can be carried out cyclically such that in each cycle a single next correct nucleotide is examined (i.e. the next correct nucleotide being a nucleotide that correctly binds to the nucleotide in a template nucleic acid that is located immediately 5' of the base in the template that is hybridized to the 3'-end of the hybridized primer) and, subsequently, a single next correct nucleotide is added to the primer. Any number of cycles can be carried out including, for example, at least 1, 2, 5, 10, 20, 25, 30, 40, 50, 75, 100, 150 or more cycles. Alternatively or additionally, the number of cycles can be capped at no more than 150, 100, 75, 50, 40, 30, 25, 20, 10, 5, 2 or 1 cycles.

Sequencing-by-synthesis (SBS) techniques can also be used. This technique generally involves the enzymatic extension of a nascent primer through the iterative addition of nucleotides against a template strand to which the primer is hybridized. Briefly, SBS can be initiated by contacting target nucleic acids, attached to features in a flow cell, with one or more labeled nucleotides, DNA polymerase, etc. Those features where a primer is extended using the target nucleic acid as template will incorporate a labeled nucleotide that can be detected. Optionally, the labeled nucleotides can further include a reversible termination property that terminates further primer extension once a nucleotide has been added to a primer. For example, a nucleotide analog having a reversible terminator moiety can be added to a primer so that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length N. Exemplary SBS procedures, reagents and detection instruments that can be readily adapted for use with an array produced by the methods of the present disclosure are described, for example, in Bentley et al., *Nature* 456:53-59 (2008), WO 04/018497; WO 91/06678; WO 07/123744; U.S. Pat. Nos. 7,057,026; 7,329, 492; 7,211,414; 7,315,019 or 7,405,281, and US Pat. App. Pub. No. 2008/0108082 A1, each of which is incorporated herein by reference. Also useful are SBS methods that are commercially available from Illumina, Inc., San Diego Calif.

Some SBS embodiments include detection of a proton released upon incorporation of a nucleotide into an extension product. For example, sequencing based on detection of released protons can use reagents and an electrical detector that are commercially available from Thermo Fisher (Waltham, Mass.) or described in US Pat. App. Pub. Nos. 2009/0026082 A1; 2009/0127589 A1; 2010/0137143 A1; or 2010/0282617 A1, each of which is incorporated by reference.

Other sequencing procedures can be used, such as pyrosequencing. Pyrosequencing detects the release of inorganic pyrophosphate (PPi) as particular nucleotides are incorporated into a nascent primer hybridized to a template nucleic acid strand (Ronaghi, et al., *Analytical Biochemistry* 242 (1), 84-9 (1996); Ronaghi, *Genome Res.* 11 (1), 3-11 (2001); Ronaghi et al. *Science* 281 (5375), 363 (1998); U.S. Pat. Nos. 6,210,891; 6,258,568 and 6,274,320, each of which is incorporated herein by reference). In pyro sequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system.

Sequencing-by-ligation reactions are also useful, including, for example, those described in Shendure et al. *Science* 309:1728-1732 (2005); U.S. Pat. No. 5,599,675; or 5,750, 341, each of which is incorporated by reference. Some embodiments can include sequencing-by-hybridization procedures as described, for example, in Bains et al., *Journal of Theoretical Biology* 135 (3), 303-7 (1988); Drmanac et al., *Nature Biotechnology* 16, 54-58 (1998); Fodor et al., *Science* 251 (4995), 767-773 (1995); or WO 1989/10977, each of which is incorporated by reference. In both sequencing-by-ligation and sequencing-by-hybridization procedures, primers that are hybridized to nucleic acid templates are subjected to repeated cycles of extension by oligonucleotide ligation. Typically, the oligonucleotides are fluorescently labeled and can be detected to determine the sequence of the template.

Some embodiments can utilize methods involving real-time monitoring of DNA polymerase activity. For example, nucleotide incorporations can be detected through fluorescence resonance energy transfer (FRET) interactions between a fluorophore-bearing polymerase and gamma-phosphate-labeled nucleotides, or with zeromode waveguides (ZMW). Techniques and reagents for sequencing via FRET and or ZMW detection are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

The methods disclosed herein also can be carried out using labeling techniques that differ from those conventionally used in other DNA sequencing protocols. For example, detectable signals indicating formation of a ternary complex preferably do not result from energy transfer between labels (e.g., fluorophores or quenchers) attached to the polymerase and any nucleotide. Generally speaking, the label or dye present on the labeled nucleotide or the labeled polymerase need not be a conformationally sensitive dye that changes spectral properties when the cognate nucleotide is present in a ternary complex. The label or dye of the detectable nucleotides employed in the procedure preferably is not an intercalating dye (e.g., as disclosed in U.S. Pat. No. 8,399, 196), that changes its signal-generating properties (e.g., fluorescent output) upon binding DNA. There is no requirement for different labels (e.g., FRET partners) to be present on two or more of: the polymerase, the primed template nucleic acid, and the nucleotide. The polymerase preferably does not transfer energy to the labeled nucleotide to render it detectable by any detection apparatus used for carrying out the technique. In certain embodiments (e.g., employing labeled nucleotides), the polymerase is unlabeled, or does not generate any signal used for identifying cognate or non-cognate nucleotide. In other embodiments (e.g., employing labeled polymerases), the nucleotide is unlabeled, or does not generate any signal used for distinguishing cognate and non-cognate nucleotides.

Optionally, the method to identify target sequences includes simply sequencing the barcode without the need to sequence the target sequences. The barcode is sequenced by hybridizing a barcode sequencing primer to the universal priming sequence contained within an RCA product, and then identifying one or more cognate nucleotides downstream of the 3'-end of the primer.

Optionally, the methods include identifying sequence variants (e.g., SNPs), using a variant sequencing primer, annealed to a specific portion of the capture pair that is adjacent to the sequence variant such that extending the variant sequencing primer produces readable sequence of the sequence variant. Optionally, a variant sequencing primer includes approximately 5-25 nucleotides (e.g., the variant sequencing primers include 10-20, or 8-15 nucleotides).

Optionally, the methods to identify sequence variants include using a variant sequencing primer to sequence the sequence variant before using the barcode sequencing primer to sequence the barcode. Optionally, the barcode sequencing primer is blocked from extension while the extension of the variant sequencing primer occurs; and is unblocked only after the extension of the variant sequencing primer has reached the end of the template. Optionally, both the barcode and the variant sequencing primers are blocked by different methods, and can be activated independently to sequence either segment first. Optionally, more than two sequencing primers are used to sequence different segments of the target nucleic acid, which can be activated sequentially to sequence the desired segments independently. Optionally, an intermediate oligonucleotide including a segment that contains a Zip barcode and a segment that hybridizes to the target is to be identified and counted. The Zip barcode on the intermediate oligonucleotide is sequenced to identify and count the target, and the SNP or variant is optionally sequenced (see, e.g., FIG. 16).

In some embodiments, digital sequencing is used, whereby each target molecule is converted into a single product which is then sequenced (i.e., individually). That is, segments of the same gene with different nucleotides at the variant position are not combined to generate a mixed or consensus sequence. The product derived from each target may include many copies of the original target sequence, as long as they are all associated with each other and able to be sequenced together. This is done to create enough copies of the template being sequenced so that they can be detected during the sequencing reaction. An example of this is a rolling circle amplification product from a target-derived circle, in which many copies of the target DNA are concatemerized and sequenced together to give a digital sequencing result. Alternatively, PCR is performed (e.g., in emulsion nanodroplets), and each target DNA is amplified and kept separate from all others by being sequestered in individual nanodroplets of the emulsion.

Provided herein are methods for identification of a sequence variant, such as a SNP. After the SNP or other sequence variants have been converted into circular nucleic acid molecules, variants, SNPs or other small genomic changes (including indels or several changed nucleotides) can be identified. The SNP (gene or allele and position) can be identified based on a Zip barcode that was specifically associated with it during library construction (e.g., picosphere formation). Optionally, the SNP and the Zip barcode are both sequenced, identifying the SNP and gene and variant position in the process. Alternatively, the circular nucleic acid molecule to be sequenced is constructed and associated with a barcode only in the presence of a particular SNP or sequence variant at a particular position in a particular location. During analysis in this example, only the barcode is sequenced, as the identity of the Zip barcode unambiguously identifies the SNP or sequence variant. In sequencing methods in which individual constructs (e.g., picospheres or circular nucleic acid molecules), can be separately sequenced, the occurrence of the Zip barcode sequences among detected nucleic acid features can be identified and counted, which represents a direct count of each SNP that was associated with it during library construction.

Optionally, a target sequence is incorporated into a circular nucleic acid molecule and RCA is performed to create a long concatemer of target sequences. A SNP sequencing primer and a barcode sequencing primer can be hybridized to the concatemer before or after the concatemer is attached to a suitable surface where sequencing will be performed. Optionally, the SNP sequencing primer is hybridized to the concatemer prior to hybridization of the concatemer to a suitable surface. Optionally, the barcode sequencing primer is attached to a suitable surface where sequencing will be performed and the concatemer is captured for sequencing by the barcode sequencing primer. The SNP sequencing primer can then be hybridized to the concatemer prior to SNP sequencing. Next the SNP itself is optionally sequenced using a primer designed to be in close proximity so that only one or a few nucleotides (e.g., in the range of from 1-10, or from 1-3 nucleotides) of sequence need to be determined. This is followed by activation of the barcode sequencing primer so that the Zip barcode sequence can be determined.

Figure 6:
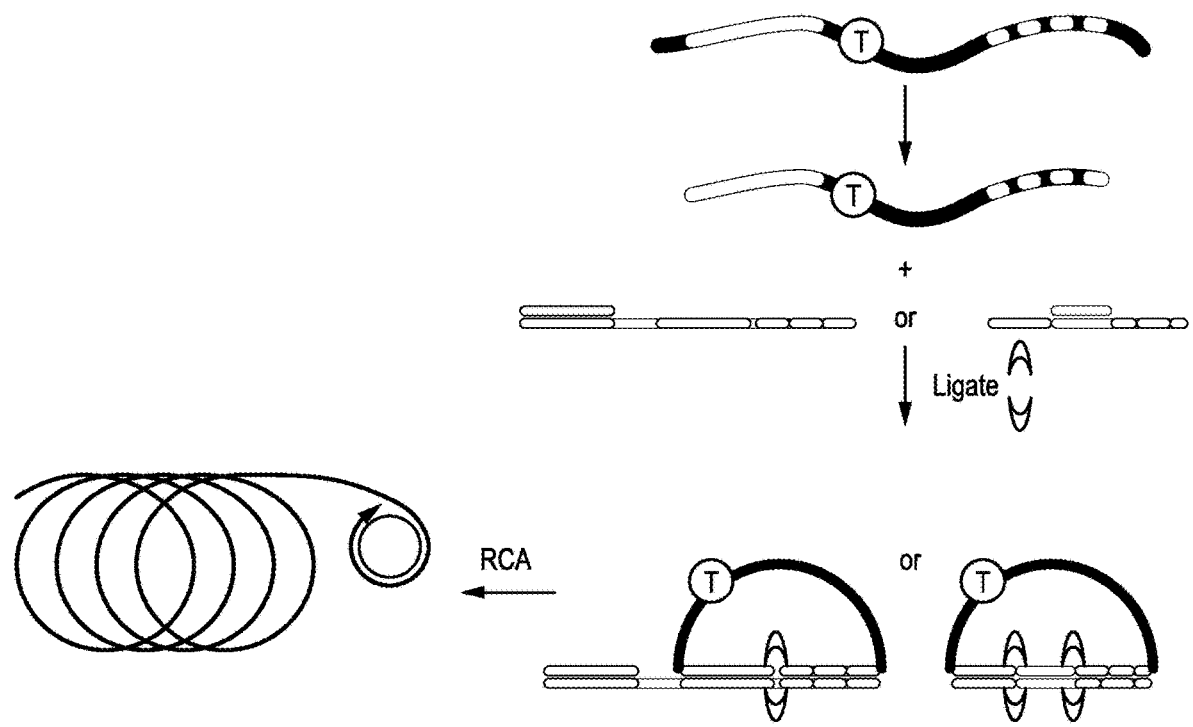
FIG. 6 is a schematic showing the circularization of a capture pair including a SNP using a sequence, and amplification of the circularized nucleic acid molecules by rolling circle amplification (RCA).

The first step is hybridization of a capture pair to the target nucleic acid surrounding the SNP or sequence variant to be determined (i.e., the SNP or the sequence variant). The capture pair is then circularized using a variety of methods. See for example, FIGS. 1, 2, 6, and 7. In FIG. 6, target DNA is first given defined ends by two cycles of primer extension (PCR). The "T" represents a SNP to be determined. After the target DNA is given defined ends by two cycles of primer extension, it is denatured and hybridized to a partially double stranded "guide sequence" (shown in gray) that aligns the 3' and 5'-ends of the target such that they can be joined by DNA ligase, thus forming a circular molecule. The guide sequence may align the ends of the target so that they ligate together, or to the 5' and 3'-end of a double stranded portion of the guide sequence. Ligation points are represented in the figures by upper and lower crescents. The circular molecule includes a primer binding site for rolling circle amplification to produce a long concatemer extension product suitable for sequencing.

In this method, unique primers and guide sequences may be required for each variant that is to be identified. If multiple variants/SNPs are present close enough to each other, a single circle generation may encompass both. The multiple variant/SNP sequences may be sequenced later with a single primer, or with multiple primers as required.

In a different kind of target circularization method, a circularization template (i.e., the capture pair) is hybridized to the single stranded DNA target such that a gap is formed surrounding a SNP or variant position to be identified in later steps (see FIG. 7). In this case the target DNA does not have to undergo primer extension to generate defined ends. The 3' arm of the capture pair hybridized to the target DNA serves as a primer for extension by a non-strand displacement, 5'-3' exonuclease-deficient polymerase. The polymerase copies the target sequence into the circular nucleic acid molecule, polymerization terminating when the polymerase reaches the 5' arm of the capture pair hybridized to the target DNA. DNA ligase is then used to join the extended strand to the 5' arm of the capture pair, thus forming a circle. The circle can then serve as a template for rolling circle amplification.

Figure 7:
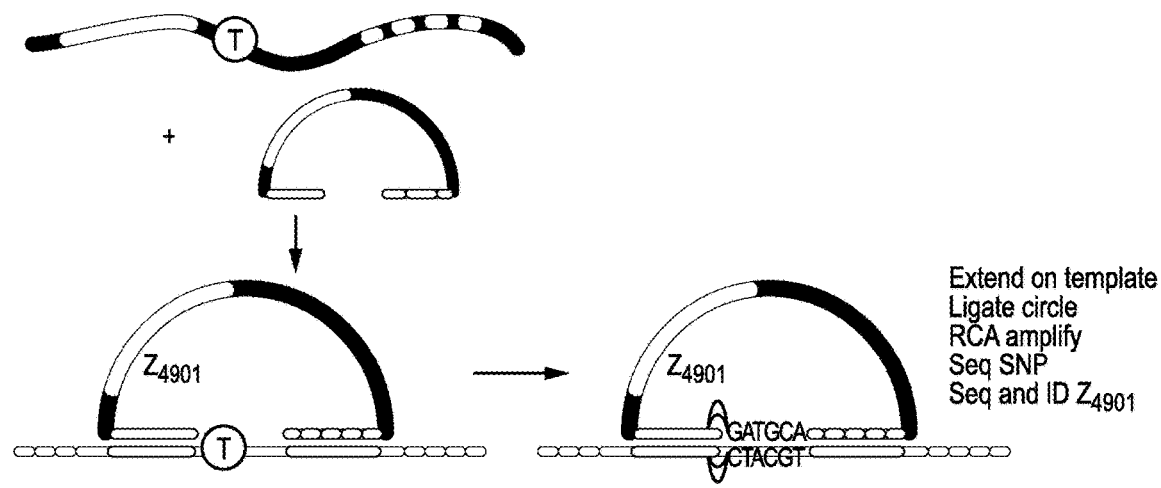
FIG. 7 is a schematic showing the incorporation of target sequence surrounding a single nucleotide polymorphism (SNP) into a circular nucleic acid molecule in a SNP dependent manner. A capture pair containing a barcode (Z4901) is hybridized to a target sequence containing the SNP. The gap between the ends of the capture pair hybridized to the target sequence is extended to fill in the gap. The circular molecule is ligated and amplified using RCA to form a picosphere. The sequence of the SNP and the barcode for each picosphere is then determined.

In FIG. 7, an optional Zip barcode segment is included, shown as "Z4901" in this example. This optional region may be separate from, or may also overlap or coincide with the target capture sequences. The purpose of the Zip barcode is to hybridize to a capture or sequencing primer, or be sequenced itself in later steps. In either case, hybridization to or sequencing of the Zip barcode region identifies this circle as being associated with the variant/SNP copied into the circularization template. Thus, the Zip barcode sequence, by itself, identifies the gene and region from which the sequence variant originated.

After circularization, the next step is sequencing to identify the sequence variant or SNP followed by sequencing of the Zip barcode. The method includes generating the amplified products using the circle as a template (e.g. to create DNA picospheres), hybridizing capture and/or sequencing primers to the amplified products, localizing the amplified products for sequencing on a surface, sequencing a first region (e.g., the SNP), sequencing a second or additional regions (e.g., the barcode), and identifying and scoring the variant/SNP and Zip barcode from the sequencing data. Optionally, only the barcode is sequenced to identify the SNP. The following description illustrates one general way of performing the method with variations. A linear concatemeric amplification product is the result of several forms of rolling circle amplification. In solution these long molecules take the form of a random coil, the size of which is dependent on length and amount of double-stranded ("ds") or single-stranded ("ss") character (i.e. fully single-stranded or double-stranded, or partially double-stranded). Fully single-stranded molecules 100,000 nucleotides in length will be approximately 0.5 μm in diameter in solution (2× radius of gyration). Fully double-stranded molecules will be much larger, for example, approximately over 6 μm in diameter for a dsDNA 100 kb long. Partially dsDNA will be intermediate in size depending on the relative amount of double-stranded and the single-stranded DNA in the molecule. For convenience, these long amplicons are referred to herein as "DNA picospheres" (or simply "picospheres") because of their random coil nature and size (see, e.g., FIG. 8).

Figure 8:
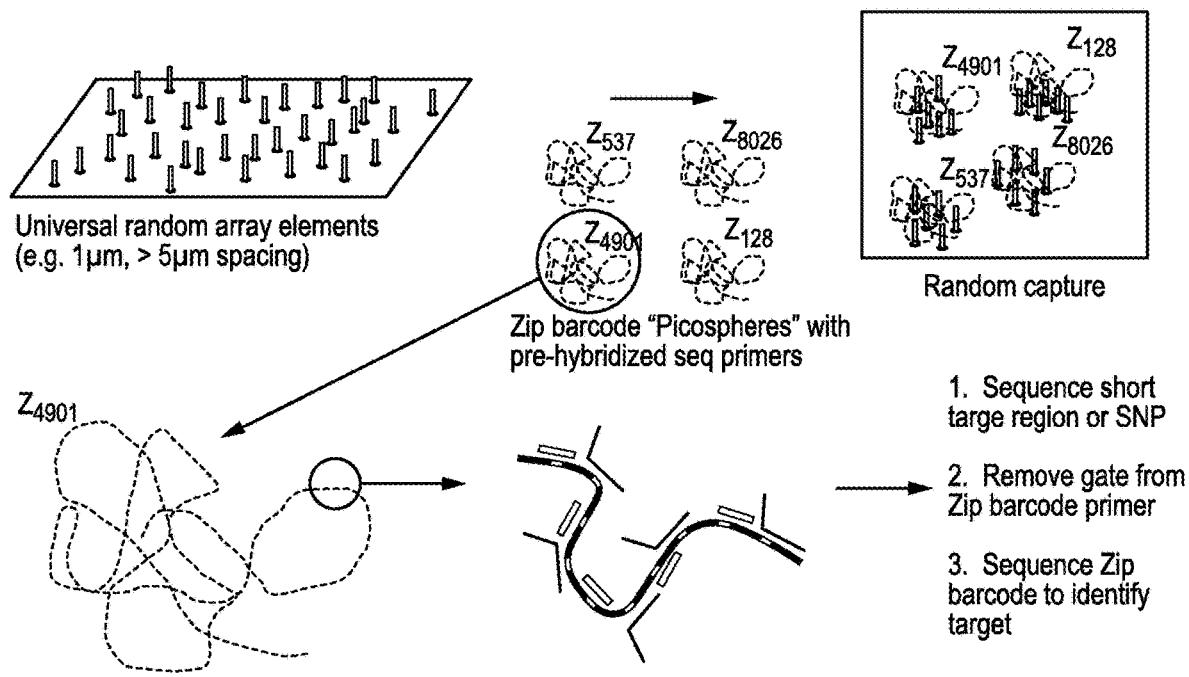
FIG. 8 is a schematic showing one scheme for immobilization of RCA products on a suitable surface to yield picospheres for sequencing. The picospheres can be pre-hybridized with sequencing primers (e.g., barcode sequencing primers and/or variant sequencing primers) and randomly captured on a suitable surface for sequencing.

During amplification or after, primers and/or capture oligonucleotides can be hybridized to the amplification products. There next can be a step that involves attaching the picospheres to a surface suitable for sequencing. The surface can be a relatively large planar substrate, or the surface of individual micron-scale beads or particles, engineered particles with identification codes, and the like. Additionally, the amplicon or picosphere may be segregated inside a nanodroplet formed in an oil emulsion so that they can be individually digitally sequenced. One example is shown in FIG. 8, in which picospheres with hybridized primers and capture oligonucleotides (thus creating a partially double-stranded DNA picosphere) is hybridized via complementary capture oligonucleotides on the surface where sequencing will be performed. The concentration of the picospheres is adjusted so that only one picosphere hybridizes to each primer cluster, which in this example are approximately 1 μm in diameter and spaced 5 μm apart. On the upper left side of FIG. 8, clusters of complementary capture primers (or barcode sequencing primers) on the sequencing surface are represented by upwardly directed bars, each of which would contain many thousands or millions of actual capture oligonucleotides attached to the surface. On the upper right side, unique picospheres generated from unique DNA targets are shown hybridized (or otherwise attached) to individual clusters (indicated by the barcode numbers, such as Z4901). In this example, the clusters include "universal capture" sequences that can capture any pico sphere. The lower part shows a close-up representation of the picosphere with hybridized oligonucleotides and primers.

Figure 9:
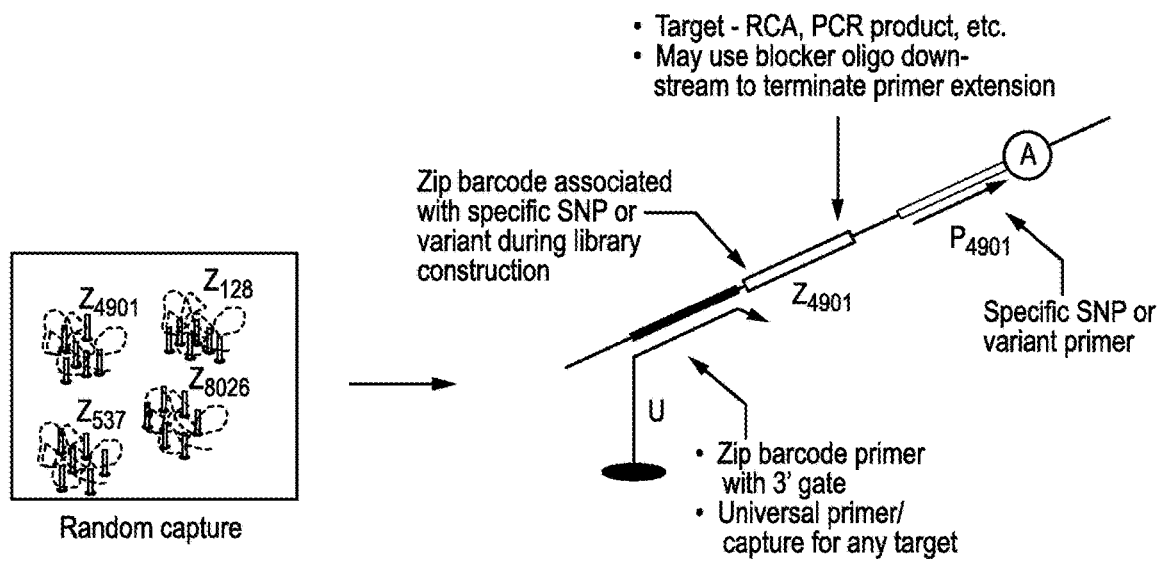
FIG. 9 is a schematic showing a picosphere bound to a surface by a barcode sequencing primer (Zip barcode primer or universal capture primer). The primer contains a 3' blocking group preventing extension of the primer, and is located adjacent to a barcode sequence (Z4901). A sequencing primer (P4901) can be used to sequence the SNP or sequence variant.

A detailed view of an example construct on the surface of a sequencing cluster is depicted in FIG. 9. In this case a segment of a picosphere generated from a circular construct, as in FIG. 7, is shown captured by a universal capture sequence on the surface, hybridized to a complementary sequence that originated in the circular nucleic acid molecule just upstream from the Zip barcode (shown as Z4901). A primer that will be able to sequence the SNP position is shown as "P4901", since it is specific for this variant region of the particular target nucleic acid which is specifically associated with Zip barcode Z4901 during library construction. Several features are important for the Zip barcode SNP sequencing process. The first is that there are two regions to sequence, the variant/SNP, and the Zip barcode. The primer that will sequence the Zip barcode is shown with a "gate" (bent arrow) that prevents it from being extended until the gate is opened or removed. The other primer for the variant/SNP is shown with a straight arrow head, indicating it has a free 3'-end and is ready to be extended and sequence the nearby variant/SNP. Either or both of the primers (and possibly additional primers) may be gated. An important feature of the gate is that it can be separately opened or removed for each kind of primer (e.g. SNP or barcode sequencing primer). In this example, the SNP sequencing primer is ready to sequence without modification. The barcode sequencing primer is shown with a 3' mismatch gate, in which one or more nucleotides are mismatches to the binding region on the target. A polymerase lacking the ability to "correct" the mismatch on the primer will not be able to extend the primer. However, the gate can be removed, for example, by using an error-correcting polymerase with 3'-5' exonuclease activity and appropriate dNTP or dNTPs.

Figure 10A:
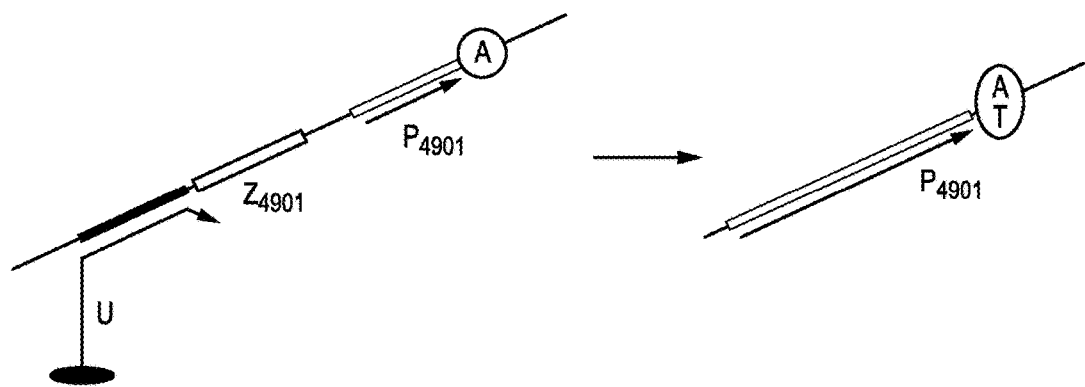
FIGS. 10A and 10B illustrate process steps for sequence or SNP determination.
Figure 10B:
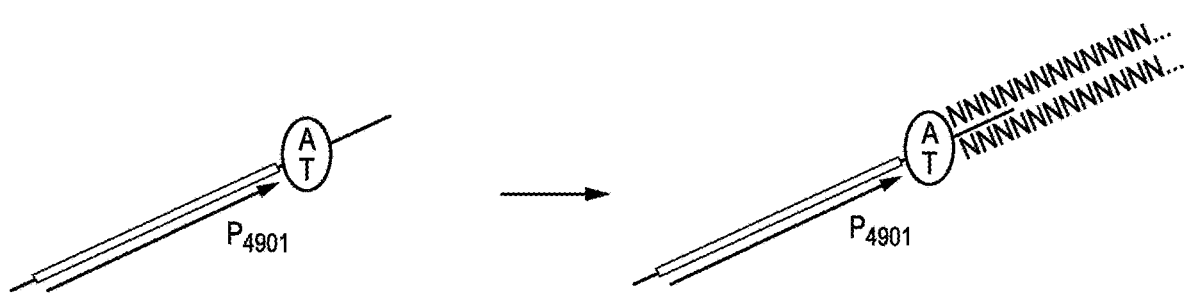

The continuation of the process can involve sequencing the first region, as indicated in FIGS. 10A and 10B. The variant/SNP sequencing primer will be positioned very close to the nucleotide or nucleotides to be sequenced, so as to require a minimum number of sequencing cycles to identify the sequence of interest. In all cases, the exact position of the SNP will be known, since it won't need to be identified by target DNA sequence context. In many cases the 3'-end of the primer will be directly adjacent to the variant/SNP nucleotide, so only one sequencing cycle is required to identify it. The example in FIG. 10A shows the SNP in the target as "A", and one cycle of extending the SNP sequencing primer P4901 incorporates and identifies a complementary "T."

The next step shown in FIG. 10B is run off extension of the SNP sequencing primer without interrogation, or any attempt to identify further nucleotides. This may extend to the end of the template, or up to a blocker oligonucleotide that cannot be displaced by the polymerase. The purpose is to end sequencing from this primer so that no nucleotides will be incorporated and interfere with sequencing from subsequent primers.

Figure 11A:
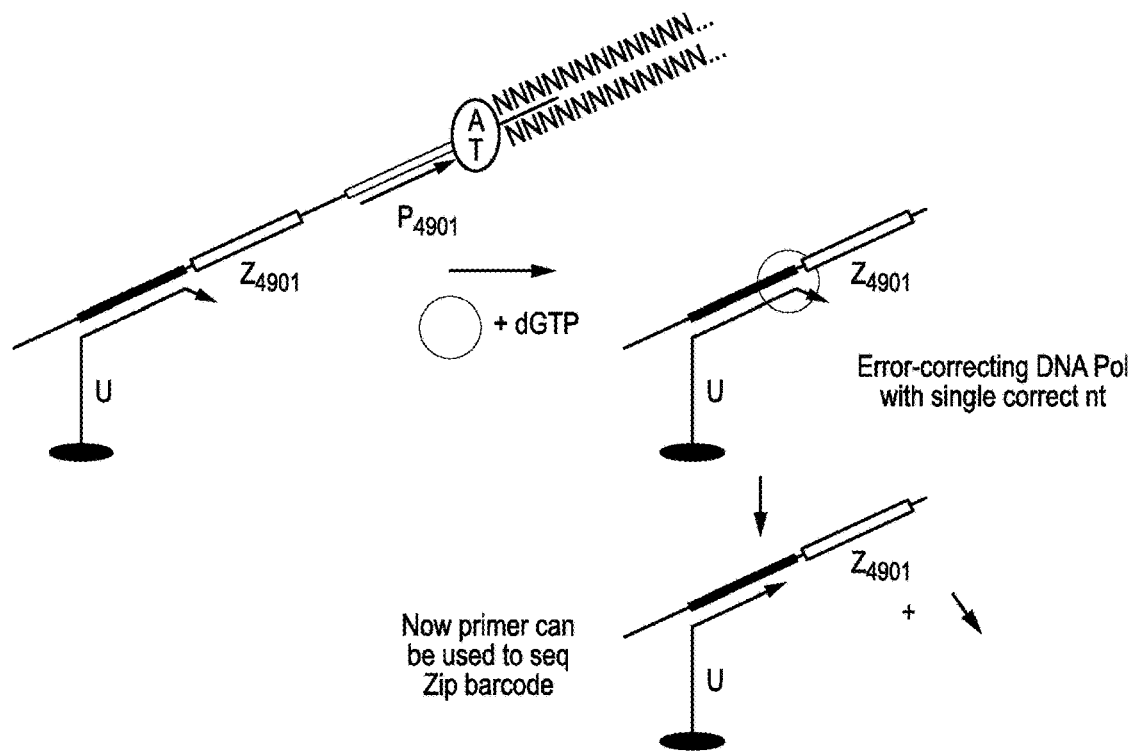
FIGS. 11A and 11B illustrate sequencing of the template shown in FIG. 10B using a second primer.
Figure 11B:
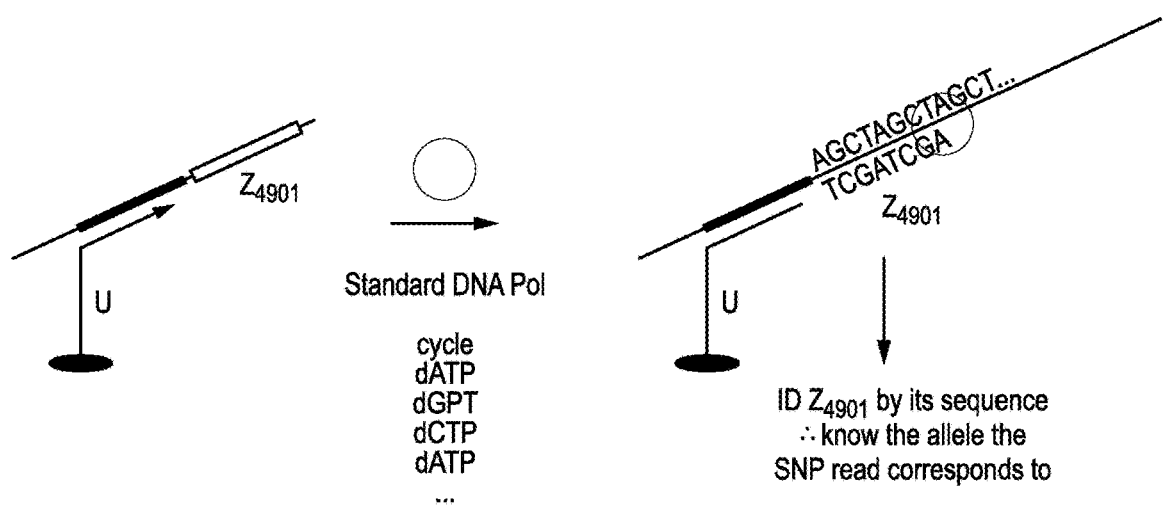

Step 5 of a Zip barcode SNP sequencing process, sequencing from at least a second primer, is shown in two parts in FIGS. 11A and 11B. The first step in FIG. 11A is to remove the gate (i.e., blocker of extension) from the barcode sequencing primer that will sequence the Zip barcode (Z4901). As described for FIG. 7, the gate is a 3' mismatch and is removed using an error correcting polymerase shown as a small circle, and a single dNTP (dGTP in this example) that is complementary for the first correctly matching nucleotide that will become the extendable 3'-end of the primer. This error correcting polymerase is removed from the system, and the Zip barcode sequence can then be determined using the sequencing polymerase (small gray circle) and cycling with individual dNTPs as shown in FIG. 11B.

Optionally, all barcode sequencing primers and corresponding hybridization regions in the amplicon or picosphere have the same configuration. Thus, the first matching nucleotide at the 3'-end of the barcode sequencing primer will be the same for all barcode sequencing primers in the sequencing reaction. Optionally, the system is configured so that the last nucleotide incorporated in the runoff of the first primer will be the same, so that removing the gate from the barcode sequencing primer will not reveal additional nucleotides in the runoff product of the first primer that could interfere with Zip barcode sequencing.

Figure 12:
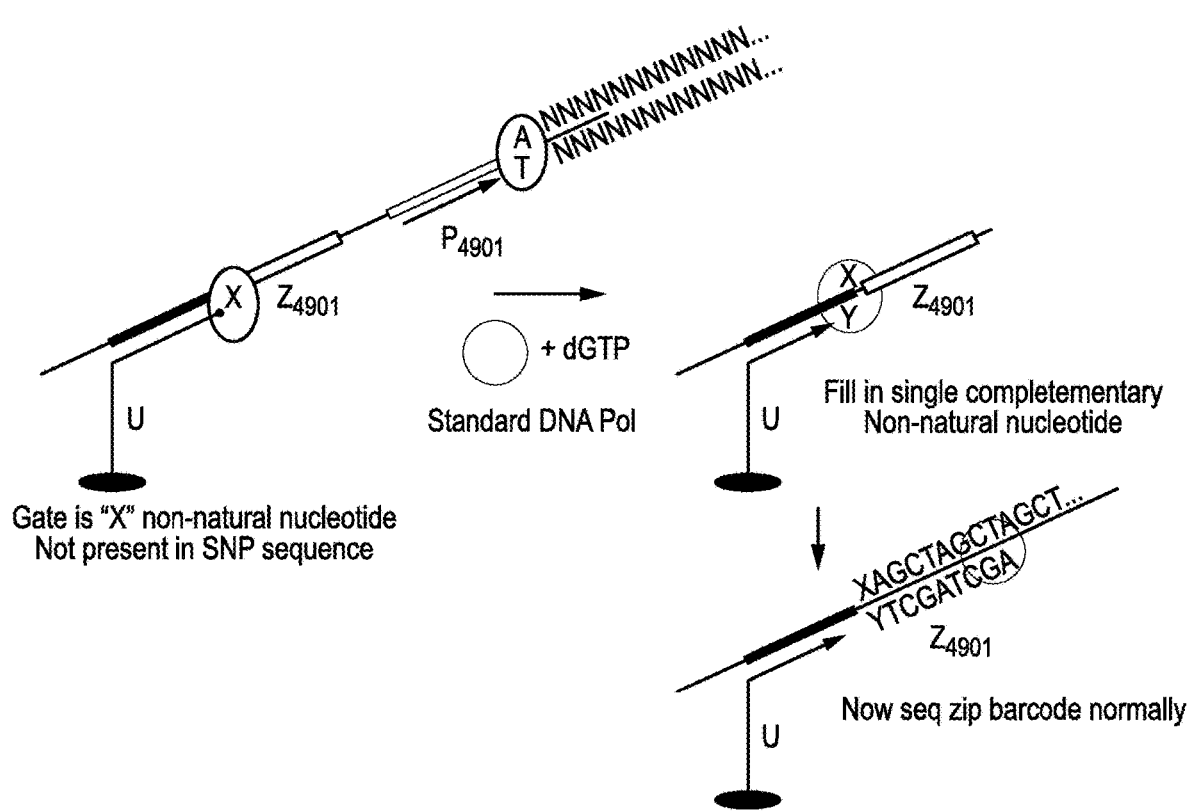
FIG. 12 is a schematic showing use of a non-natural nucleotide ("X") to prevent extension of the barcode sequencing primer. Upon addition of a non-natural nucleotide ("Y") complementary to non-natural nucleotide "X", the barcode (Z4901) can then be sequenced. Polymerase is indicated by an open circle.

There are many ways to create a gated primer that can be selectively activated. In addition to activating a single gated primer with one of these methods, it would also be possible to activate several gated primers in sequence using several of gating methods. Additionally, but using several of these methods in combination, it would be possible to generate a very large number of different gates that could be activated individually and selectively. FIG. 12 shows how non-naturally occurring nucleotides can be used to prevent extension during normal nucleotide sequencing of a proceeding primer. In this example, non-natural nucleotides called "X" and its complement "Y" (see Malyshev et al. PNAS 109: 12005-12010 (2012)) are used.

Since X and Y do not exist in naturally occurring DNA, they are not included in the sequencing interrogation and extension cycling reactions. On the left side of FIG. 12, this is shown as the "U" primer that is just upstream of the Z4901 Zip barcode region. The X nucleotide was incorporated into the target to be sequenced for example a synthetic oligonucleotide that captures the DNA target, or incorporated into the RCA product from the circularization template. During sequencing of the variant/SNP from the P4901 primer using natural nucleotides, the U primer will not be extended. Following completion of sequencing from the first primer, the gate on the U primer is opened by a single nucleotide extension with dYTP. Once Y is incorporated and primer U is activated, sequencing of the Z4901 Zip barcode can be performed normally with natural nucleotides (right side of FIG. 12).

Figure 13:
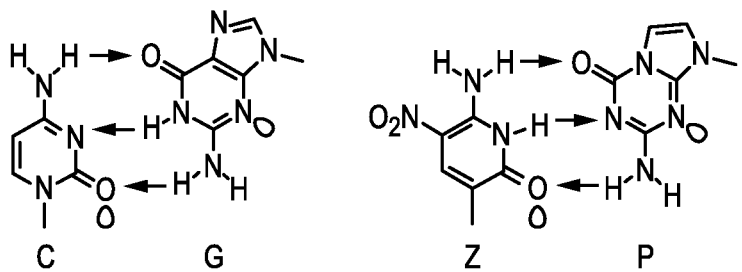
FIG. 13 is a schematic showing three exemplary non-natural nucleotides suitable for use in the provided methods. Free electron pairs are indicated at certain oxygen (O) and nitrogen (N) positions.
Figure 13:
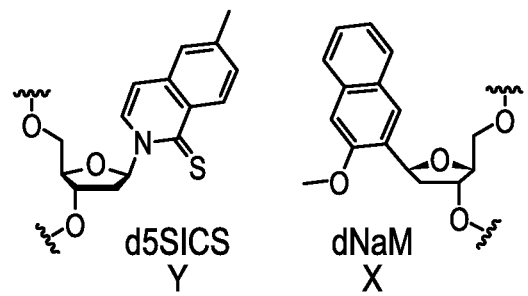
Figure 13:
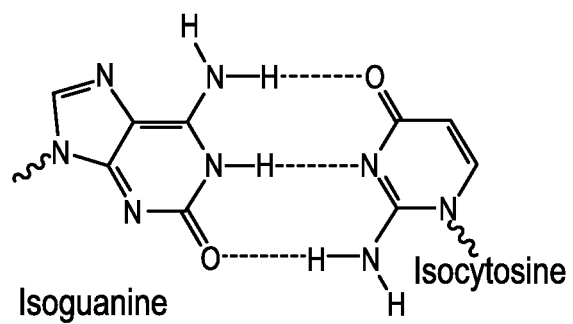
Figure 14:
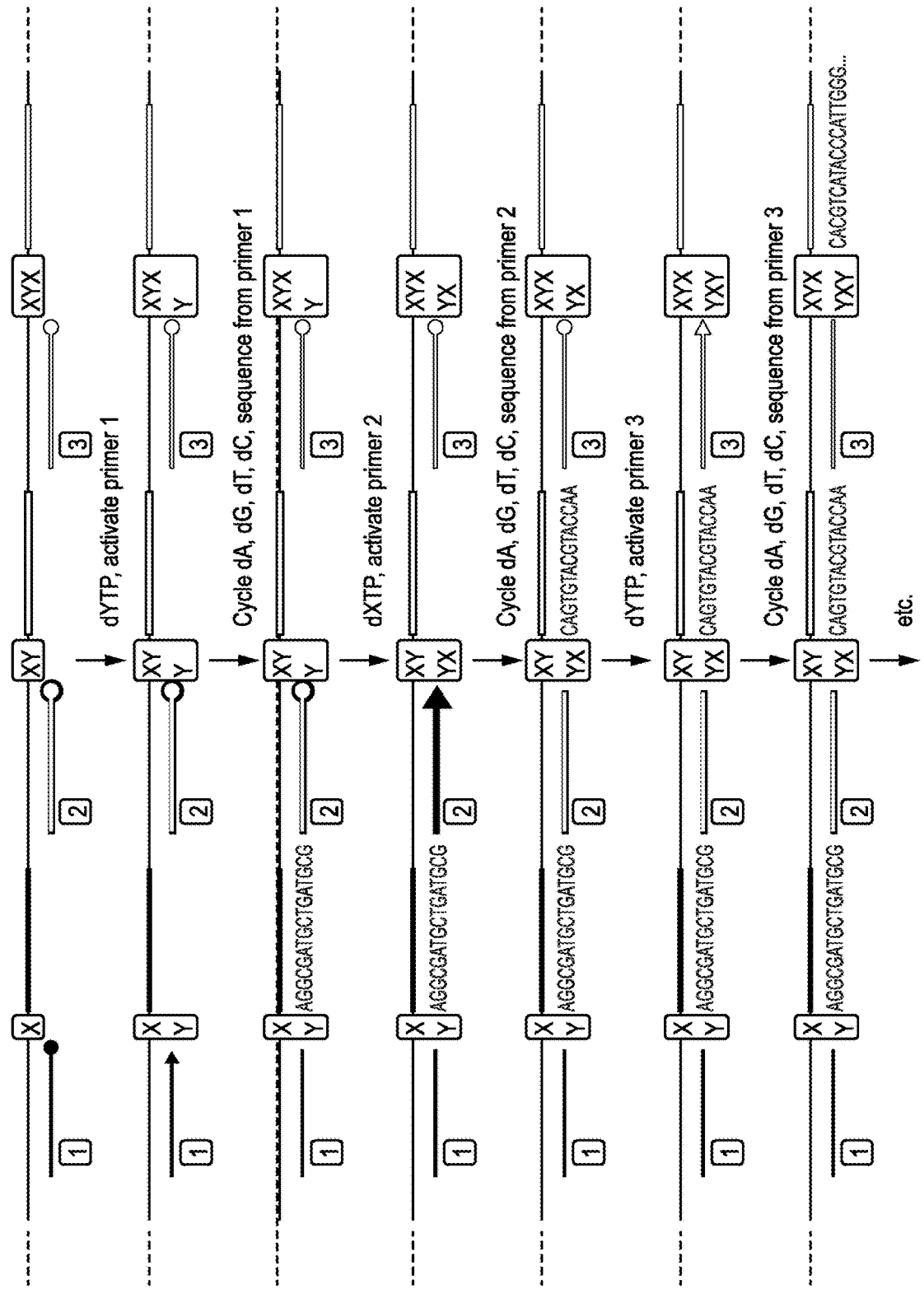
FIG. 14 is a schematic showing the use of different non-natural nucleotide combinations to sequence different portions of a target nucleic acid.

Three examples of suitable non-natural nucleotides suitable for this application are shown in FIG. 13. As stated above, it is possible to generate a large number of gates that can be specifically and sequentially activated by using combinations of non-natural dNTPs that must be filled in by polymerase in order to provide a 3'-end that can then be used to sequence with normal dNTPs. One simple way to do this is to have several primers, all with gates using X and Y nucleotides in the pattern gate 1=X, gate 2=XY, gate 3=XYX, gate 4=XYXY, gate 5=XYXYX and so on for as many sequentially activated primers as are required at a single or multiple sequencing sites. This example is shown in FIG. 14, where three primers have gates X, XY, and XYX. Inactive (blocked) primer states are represented by a circle on the 3'-end of the primer, and activated (gate opened) primers are shown with an arrow. The first primer can be activated by incorporating a Y nucleotide across from the X nucleotide in the target. Because of the way the primer gates are designed, each gets a non-natural nucleotide incorporation at each step, so only one additional non-natural nucleotide incorporation is needed to activate the next primer. Thus, all primers will incorporate Y, but only the first primer is activated. Sequencing can then be performed with natural nucleotides from the first primer. All other primers require at least one additional non-natural nucleotide to be incorporated before being activated, so they remain inactive. The second primer can be activated similarly by incorporating an X nucleotide across from the Y in its target sequence. Now the second primer is activated and able to incorporate natural nucleotides complementary to the target sequence downstream from the gate. Sequencing is then performed with natural nucleotides from the second primer. All other primers require at least one additional non-natural nucleotide to be incorporated before being activated, so they remain inactive. The third primer can then be activated by incorporating a Y. Sequencing from the activated third primer can be performed with natural nucleotides.

The process can be continued for as many primers as necessary. Since at least some primers need to be activated in this scenario, it is not more difficult to design the system so that all primers need to be activated. This might also be preferable, since it ensures that primers can only be extended when specifically needed; and gives added flexibility to library preparation, sequencing chemistry and instrumentation design.

Figure 15:
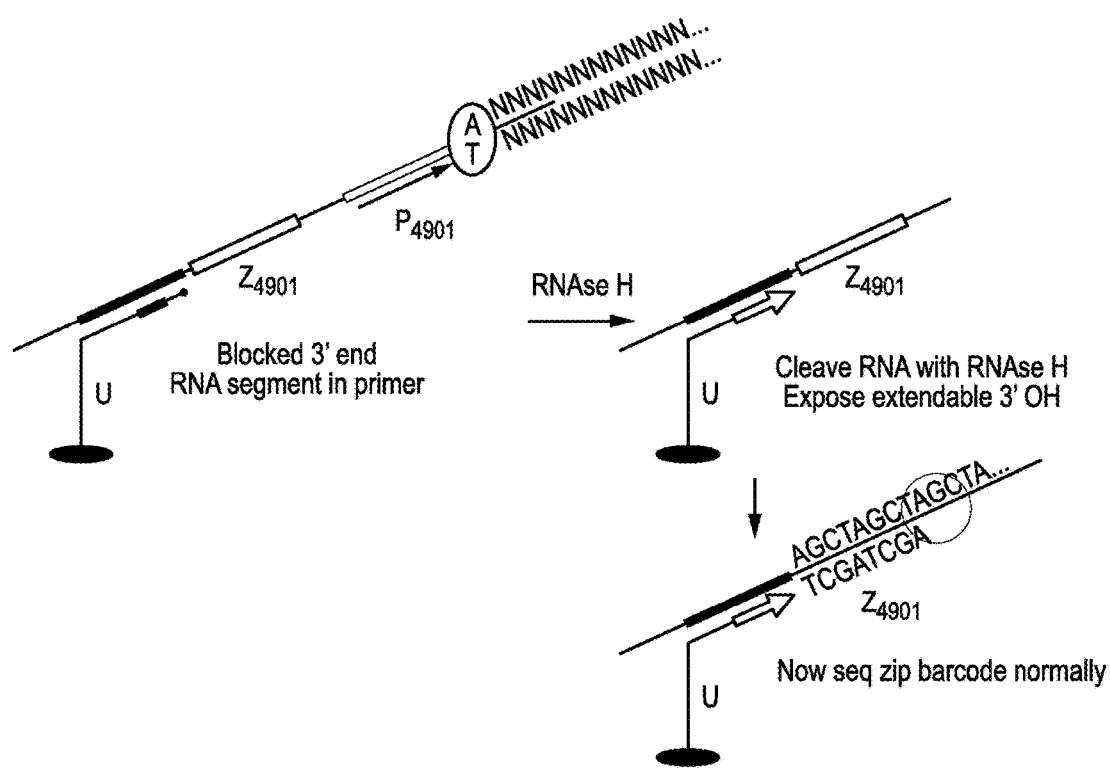
FIG. 15 is a schematic showing a 3' blocked barcode sequencing primer including an RNAseH site within the primer ("RNAse H gate"). RNAse H can be used to cleave the primer at this site allowing the barcode sequencing primer to be extended to sequence the barcode (Z4901). Polymerase is indicated by an open circle.

Another example of an alternative gate is an RNAseH site within the primer (FIG. 15). The RNAseH site consists of a short segment of RNA within the blocked secondary sequencing primer that hybridizes to the DNA target to be sequenced. This RNA:DNA hybrid is a natural substrate for RNAseH endonucleases that can specifically cleave the RNA, leaving a 3' OH that can be extended by DNA polymerases. Further, since the gate of the additional primer or primers are activated by internal cleavage of the RNA portion, the 3'-end (in this example a universal capture primer) can be irreversibly or reversibly blocked.

As with the other methods shown herein, the universal capture oligonucleotide/primer is hybridized to the target to be sequenced just upstream of the Zip barcode (Z4901). As well, in the first step the variant/SNP nucleotide or nucleotides will be sequenced from the unblocked primer P4901. The optional second step is to complete extension of the unblocked primer so that no nucleotides will be incorporated and interfere with sequencing from subsequent primers. The third step is to activate the secondary primer or primers by cleavage of the RNAseH site. This leaves an extendable 3' OH, depicted as an arrow in FIG. 15. Finally, the Zip barcode (or other sequence) is determined as usual.

Figure 16:
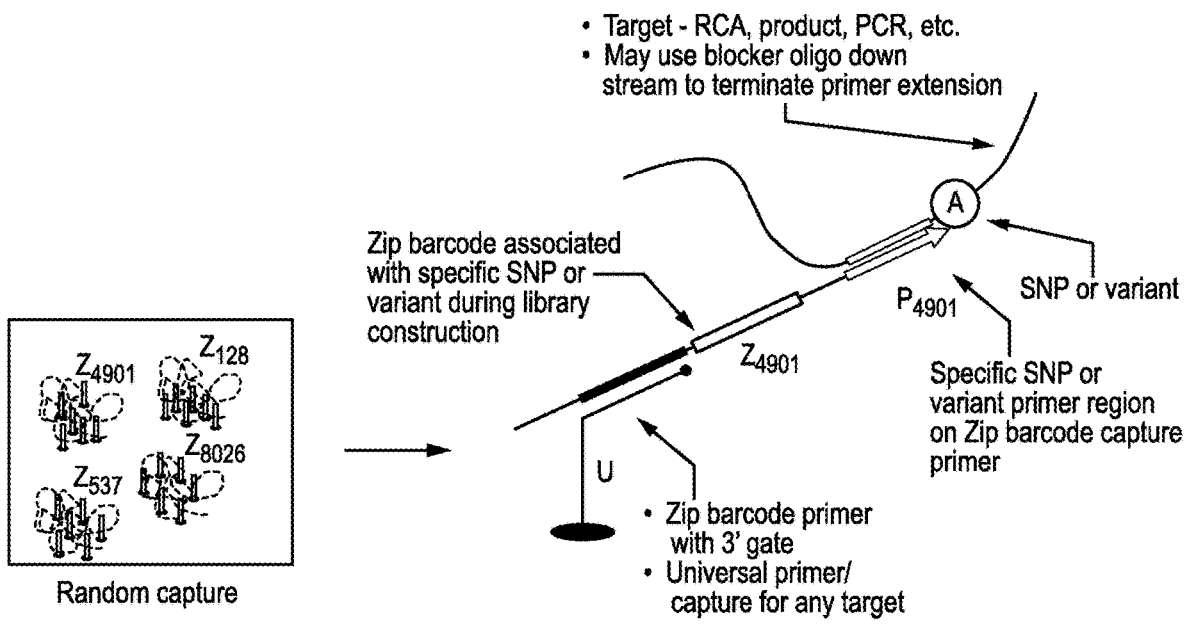
FIG. 16 is a schematic showing a Zip barcode primer or barcode sequencing primer that hybridizes to a portion of a target capture primer including a barcode and a primer specific for a target nucleic acid in proximity to a sequence variant or SNP (e.g., a variant specific primer). The intermediate target capture and sequencing primer contains the barcode, rather than the amplified circular molecule. The target nucleic acid sequence including the sequence variant or SNP is capable of hybridizing to the target capture primer including the barcode. The target nucleic acid sequence can be the amplified circularized capture pair, referred to as a "picosphere." The sequence variant or SNP can be sequenced first, followed by removal of the 3' block or 3' gate on the universal capture sequence and sequencing of the barcode (Z4901).
Figure 17:
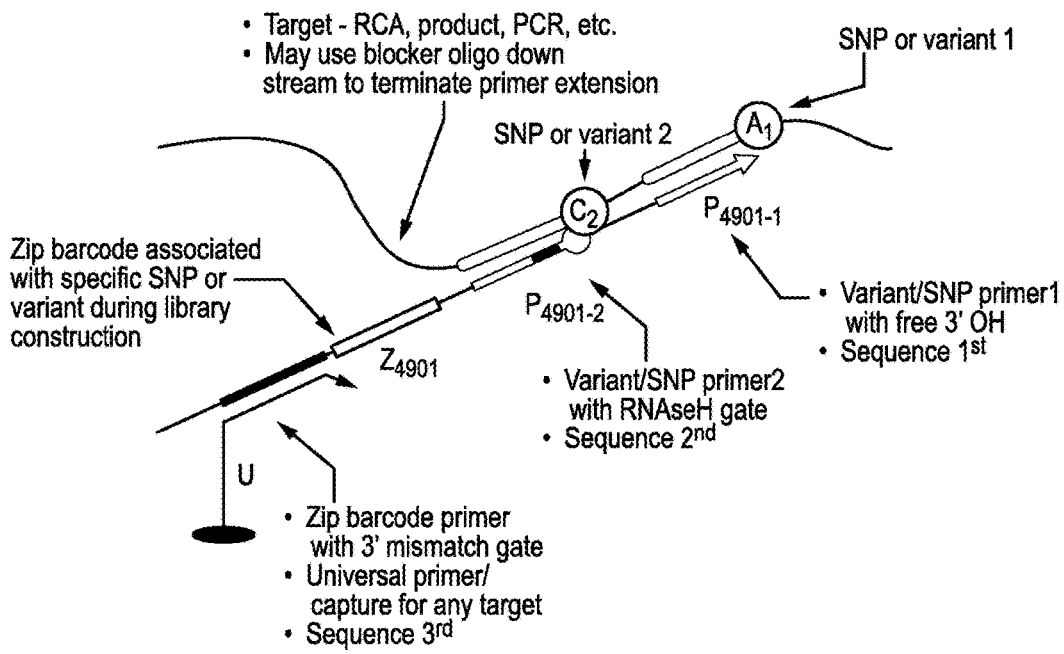
FIG. 17 is a schematic showing a barcode sequencing primer or Zip barcode primer located on a suitable surface. The barcode sequencing primer is capable of hybridizing to a target capture primer including a barcode (Z4901), a first primer capable of hybridizing in proximity to a first sequence variant or SNP and a second primer capable of hybridizing in proximity to a second sequence variant or SNP. The first primer for the first variant is capable of sequencing without prior activation. The second primer includes an RNAseH gate at its 3'-end. The second sequence variant or SNP can be sequenced following cleavage of the second primer using RNAse H to release the first primer and create a free 3' hydroxyl. Finally, the barcode can then be sequence following removal of the 3' block or gate on the barcode sequencing primer.

In some instances, it may be desirable to place the Zip barcode on an intermediary capture nucleic acid or target capture primer (as shown in FIGS. 16 and 17). The intermediary nucleic acid may contain sequences that hybridize to one or more targets, sequences that hybridize to another nucleic acid primer immobilized on a surface, one or more Zip barcode sequences, one or more primer gates that can be independently activated so that one or more targets can be sequenced after activation, and the like. Advantages include improved hybridization kinetics between the target molecule, the intermediary capture nucleic acid and an immobilized surface.

The ability to "re-program" hybridization between a target and a primer immobilized on a surface simply by changing the hybridization sequences on the intermediary nucleic acid also is possible. The ability to re-program the Zip barcode (e.g. making it shorter, longer, different, combining codes for different targets, and the like) that is associated with a particular target or immobilized capture nucleic acid is possible. Further, the intermediary nucleic acid molecule can be engineered to include multiple gated primer regions that can be hybridized to different regions on at least one target and activated in succession to sequence regions of at least one addition target or region.

An example of such an intermediary nucleic acid molecule is shown in FIG. 16. In this example the intermediary molecule contains both the Zip barcode that will be sequenced to identify the target variant/SNP, and a primer region that hybridizes to the DNA target in position to sequence the variant/SNP of interest as in the other examples described above.

FIG. 17 shows an example of a different intermediary molecule design with three primer regions. The first primer region is not gated, and hybridizes to the target to sequence the first variant/SNP without need for activation. The second primer region has an RNAseH gate, and hybridizes to the second variant/SNP primer binding region. This primer is activated second by RNAseH, then the sequence of the second variant/SNP is determined. The third primer in this example is the universal sequencing primer for the Zip barcode. In this example, the gate is a mismatch; after repair of the mismatch with 3'-5' exo (DNA pol or single-stranded exonuclease for example), the Zip barcode is sequenced using any desired technique.

The general features of the intermediary capture primer or target capture concept can be expanded and supplemented as required. For example, an arbitrarily large number of gated primers can be added, such as by using the "XYXY . . . " method with non-natural nucleotides as described above. Alternate Zip barcodes or capture regions can be added. Recognition sites for nucleic acid binding proteins or enzymes can be added to either be detected, or modify the target capture primer or target as required.

Figure 18:
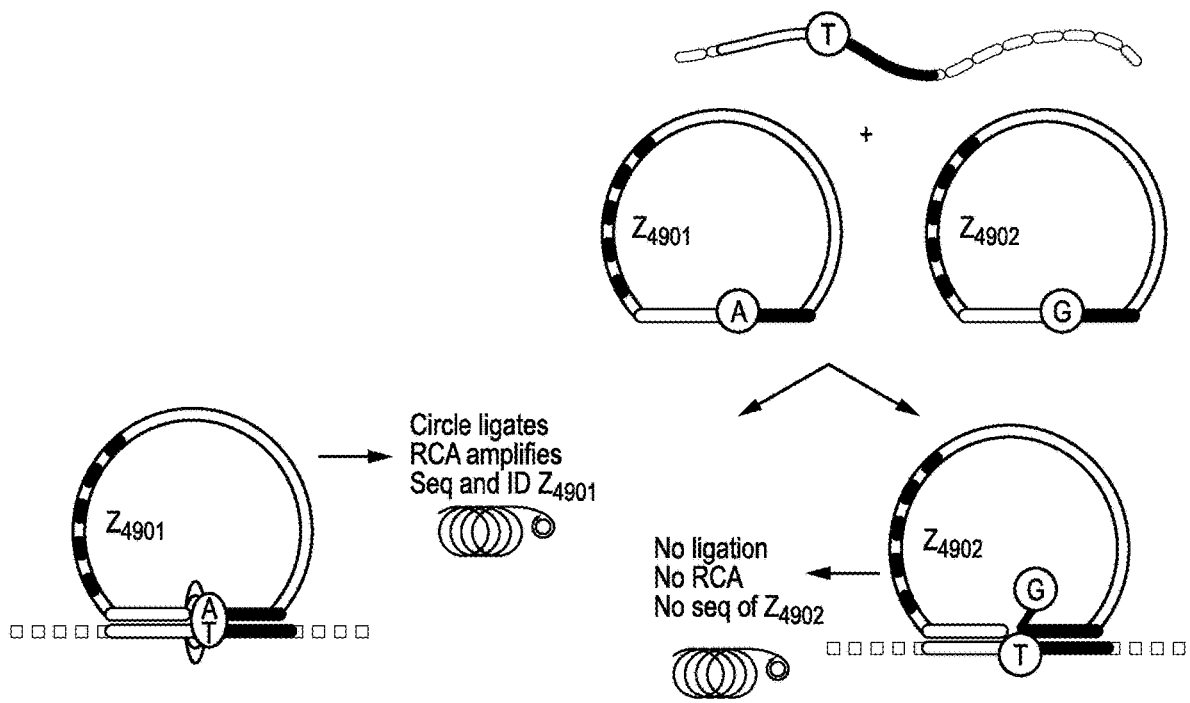
FIG. 18 is a schematic showing SNP-dependent circularization of a capture pair by ligation. Circle formation for RCA is dependent on ligation, which only occurs with a correct match. Thus, only ligated targets amplify and are sequenced. Since the barcode corresponds to the SNP, the barcode score equals the number of alleles with the corresponding SNP.
Figure 19:
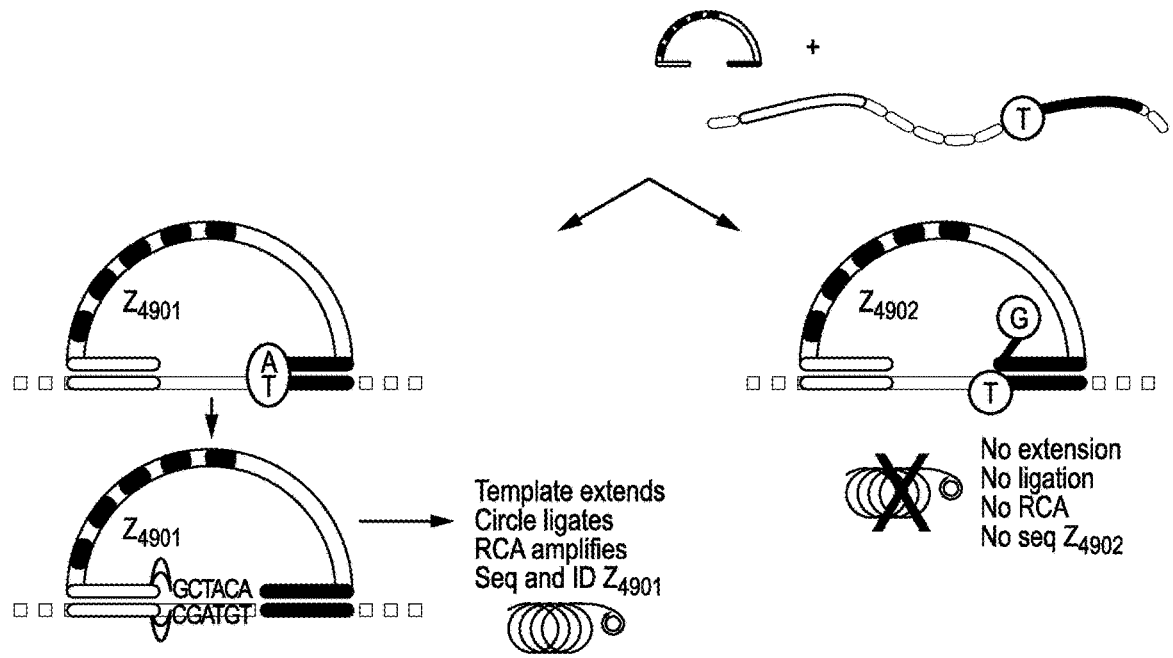
FIG. 19 is a schematic showing SNP-dependent circularization of capture pairs by extension. If the sequence on the capture pair is complementary to the SNP, the sequence can be extended and ligated to circularize the capture pair. If the sequence on the capture pair is not complementary, the capture pair will not be extended and, thus, not ligated or amplified. The barcode can then be sequenced and the barcode score equals the number of alleles with the corresponding SNP.

For methods including sequence variant dependent amplification and/or ligation, circularization only occurs in the presence of the anticipated nucleotide at the key variant or SNP position (see FIGS. 18 and 19). The Zip barcode is associated with a particular variant/SNP during circle construction. Thus, a particular SNP nucleotide variant is associated with a particular Zip barcode. Sequencing the Zip barcode reveals the identity of the SNP from which the circular nucleic acid molecule was constructed. Determining identity of the SNP by sequencing the SNP is unnecessary, and preferably is avoided. After circularization, similar to methods discussed previously, only successfully circularized capture pairs will be competent RCA templates, and form amplicons from which the Zip barcode can be sequenced. Circular capture pairs that were not formed because the DNA target sequence with its specific SNP was not present in the sample, cannot be amplified and therefore will not be sequenced.

FIG. 18 illustrates a method in which ends of the circularization capture pair hybridize to a DNA target such that the ends that can be ligated to form a circle are adjacent to each other, but either the 5' or 3' terminus (or within a few nucleotides from the terminus) is placed in contact with a SNP nucleotide position to be tested. A DNA ligase enzyme is selected in which its ligation activity is dependent on a hybridization match on between adjacent 3' and 5'-ends of the template and the DNA target. In FIG. 18, the target and circularization capture pair hybridize to each other. Circularization capture pairs contain a Zip barcode encoding the template specifically for the SNP nucleotide that will allow it to become circularized. As shown, the end nucleotides differ by a single SNP position in capture pairs that contain Zip barcodes Z4901—specific for a "T" at the SNP position—or Z4902—specific for a "C" at the SNP position. In this example, the DNA target being tested has a "T" at the SNP position. While both capture pairs will hybridize to target sequences, only capture pairs with Z4901 ligate to form a circularized RCA template. The remainder of the reaction is carried out as already described, in which the circularized template undergoes RCA, creates a long concatenated extension product, from which the Zip barcode regions are sequenced and counted. As indicated above, the SNP region need not be sequenced because the presence of the extension product amplicon indicates that the associated SNP at that locus was present for circularization to occur.

As shown in FIG. 19, SNP-dependent extension by DNA polymerase can be used instead of SNP-dependent ligation. In this case, the SNP-dependent position of the circularization template occurs on the 3'-end. Capture pairs hybridize to both alleles of a target sequence, but in this example only the circularized template with an "A" on the 3'-end (containing Zip barcode Z4901) that is complementary to the "T" SNP in the target will be extended by DNA polymerase. Extension terminates when the polymerase reaches the 5'-end of the template also hybridized to the target, then ligation can occur to form the circularized capture pair for RCA. Conditions can be used in which polymerase extension with 4 dNTPs and ligation can occur in the same reaction.

Figure 20:
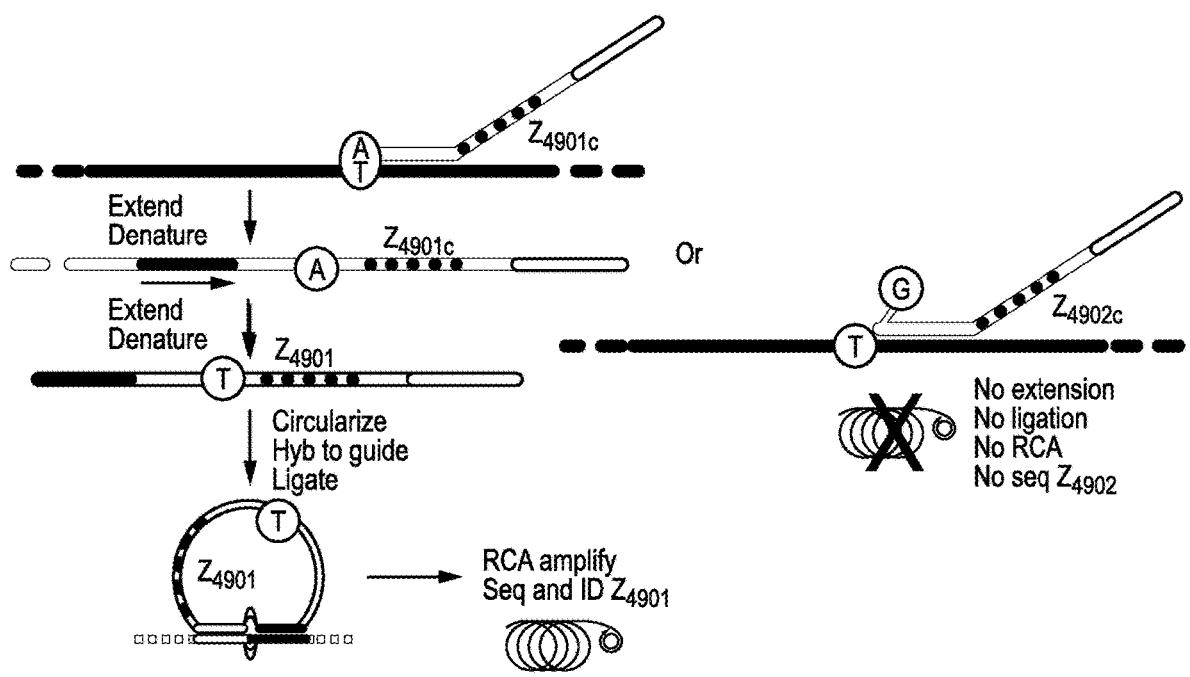
FIG. 20 is a schematic showing sequence variant or SNP-dependent circularization of a capture pair including a barcode (Z4901). The capture pair is formed by extension of two primers on the target DNA. Extension of either or both can be made dependent on a match to the SNP or other variant in the target. The first segment primer of the capture pair is extended in the presence of the correct match, followed by denaturation, hybridization and extension of the second segment primer on the extension product of the first segment. This forms a molecule including the capture pair, the variant and the barcode. Ligation of the molecule can occur through the use of a guide oligonucleotide. The circularized capture pair is then amplified and the barcode is sequenced. The barcode score equals the number of alleles with the corresponding SNP.

Optionally, sequence-dependent (e.g., SNP-dependent) circularization occurs by formation of a circular nucleic acid molecule based sequence- or SNP-dependent primer extension of two primers (e.g., upstream capture sequence and downstream capture sequence of a capture pair) separated from each other by a distance on the DNA target selected to optimize assay performance. At least one of the primers will include a SNP-specific 3' nucleotide for the locus being amplified. FIG. 20 shows, in a first step, a SNP-specific primer hybridizes to the DNA target. In addition to the 3' SNP-specific nucleotide, the primer contains an associated Zip barcode sequence and a segment complementary to part of a guide sequence. Since the 3'-end of this primer is a match with the SNP position in the DNA target, it will be extended. In the next step, the extension product and DNA target are denatured, and a second primer is hybridized to the extension product at a region that is also complementary to a second part of the guide sequence. This second primer is extended, which then creates the linear capture pair with two segments on the 5' and 3'-ends that are complementary to a guide sequence, a Zip barcode, the SNP position, and a segment with the same sequence as the original DNA target between the SNP and the second primer binding region. This extension product is denatured from the DNA target, and then hybridized to the guide sequence, which is designed to bring the ends of the extension product or linear capture pair together so that they can be ligated to form a circular nucleic acid molecule. If the primer designed for a particular DNA target locus cannot hybridize or extend, the circularized template will not be formed. For example, if the first primer has a mismatch with the SNP position, as described on the right side of FIG. 20, the primer will not be extended, and will therefore not be able to form a circular nucleic acid molecule, and so cannot be amplified and sequenced.

Figure 21A:
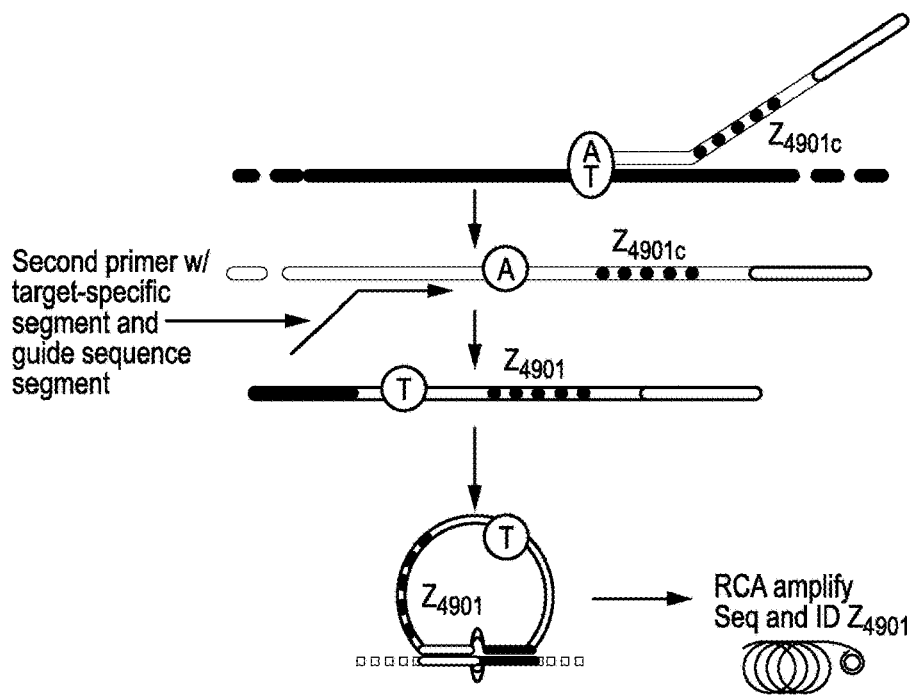
FIGS. 21A and 21B are schematics showing options to the method shown in the schematic of FIG. 20.

For example, FIG. 21A shows a modification of the method shown in FIG. 20 in which the second primer also contains a sequence complementary to the guide sequence in addition to a sequence complementary to the target. In this method, the same guide sequence can be used to circularize multiple or all linear capture pairs.

Figure 21B:
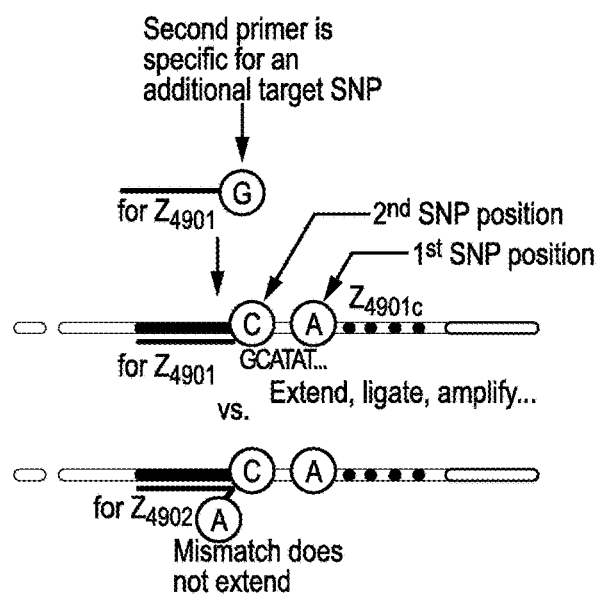

Optionally, the 3'-end of the second primer is also specific for a sequence variant/SNP in the DNA target (see FIG. 21B). The utility of this configuration is that two separated SNPs can be interrogated without having to sequence either of them. The Zip barcode that associates with primers during circle construction can be used to identify both sequence variants. The second primer that will be associated with Zip barcode Z4901 has a "C" on its 3'-end, while the second primer specific for a different allele of that target (associated with Zip barcode Z4902) has an "A." Only the SNP-specific primer for Z4901 containing a 3' "G" will be extended, and thus be able to form a circular template for RCA and sequencing according to the process in FIG. 20.

Optionally, circular nucleic acid molecules for Zip barcode sequencing which do not depend on particular target sequences (e.g., SNPs at a target locus), can be generated. Pre-formed circular nucleic acid molecules are contacted with the target, but can only be amplified by RCA when the target hybridizes to the circles and is processed to form an extendable 3'-end. Schematics of these methods are depicted in FIGS. 22-24.

Figure 22:
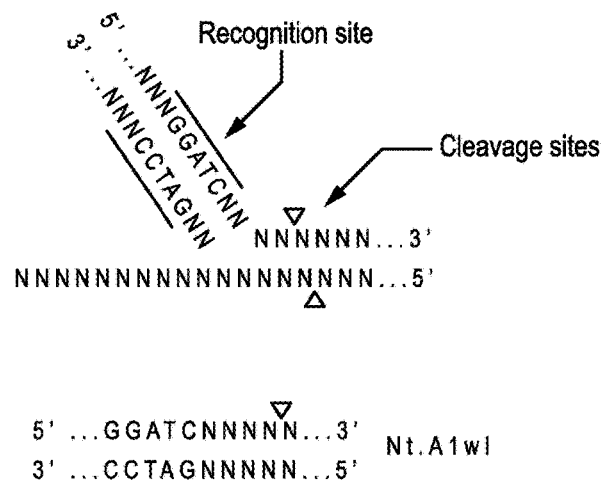
FIG. 22 is a schematic showing two methods of creating a primer from a circular nucleic acid molecule. The first is to use a normal or nicking restriction endonuclease that has a recognition sequence on one double-stranded segment of the target and cleaves a second double stranded segment of the target both segments having only one strand. The second method uses a nicking endonuclease that cleaves only one strand of the double-stranded circular nucleic acid molecule. Upon cleavage, a 3'-5' single-stranded specific exonuclease can be used to digest the cleaved circular nucleic acid molecule to form a single stranded portion of the circular molecule and, thus, a free 3' hydroxyl that can serve as a primer.
Figure 23:
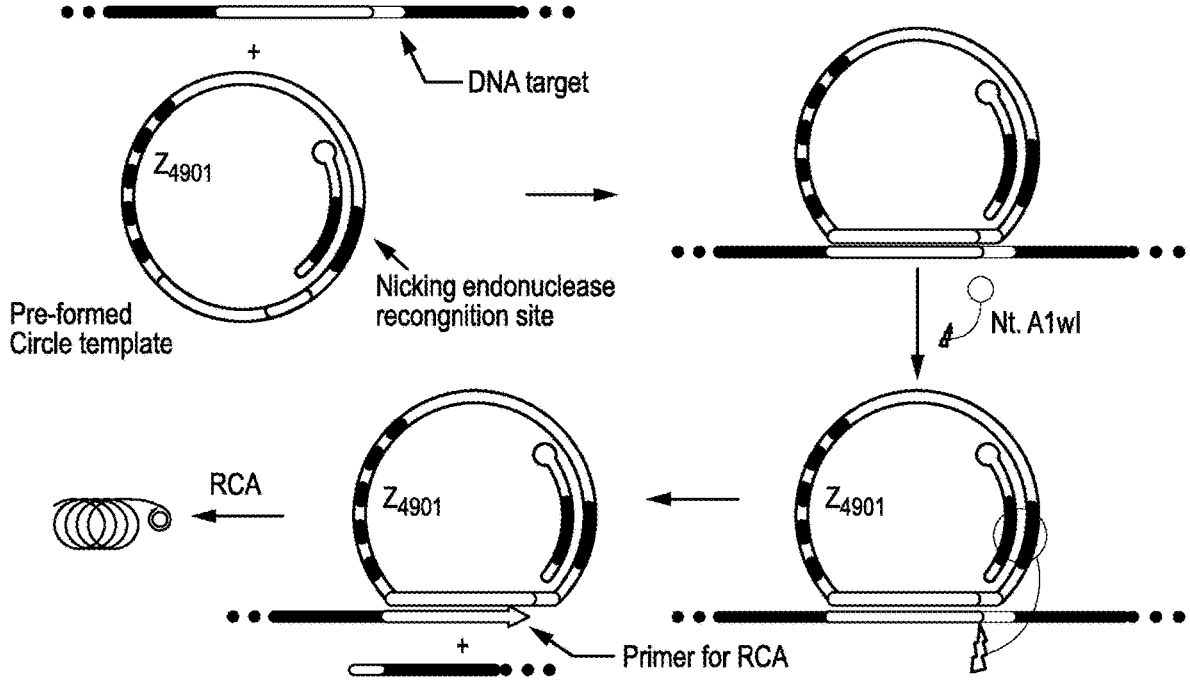
FIG. 23 is a schematic showing a pre-formed circular capture pair that contains a double stranded recognition site for a nicking endonuclease, Nt.Alw I (tethered open circle), and a hybridization region for a target nucleic acid or DNA target. The double stranded recognition site contains a block at its 3'-end to prevent its use as a primer. The pre-formed circular capture pair and DNA target hybridize to each other such that the double stranded nicking endonuclease recognition site is adjacent to the hybridized DNA target. The DNA target is then cleaved using the endonuclease resulting in primer formation for RCA.

The first example utilizes two properties of restriction endonucleases shown in FIG. 22, which are combined into a construct and processed as shown in FIG. 23. Some restriction endonucleases with separated recognition and cleavage sites can bind to their recognition site on one double-stranded segment and cleave another that is contiguous through only one strand (top of FIG. 22). Further, some modified restriction endonucleases, such as Nt.AlwI (NEB #R0627) have been engineered to cleave only the top or bottom strand four nucleotides distal to their asymmetric recognition site, and are thus termed "nicking endonucleases" (bottom of FIG. 22).

As shown in FIG. 23, provided is a pre-formed circle that contains a double stranded recognition site for a nicking endonuclease and a hybridization region for the DNA target. The pre-formed circle and DNA target hybridize to each other such that the nicking endonuclease recognition site is adjacent to the hybridized target where the DNA target will be cleaved. The nucleic acid segment which makes the recognition site double stranded should have a blocked 3'-end so that it cannot serve as a primer. In the example, Nt.Alw I binds to the recognition site in the circle, then cleaves only the DNA target, leaving a single stranded region of the circle that previously was hybridized to the DNA target. Since the 3'-end of the cleaved DNA target is hybridized to the circle, it now forms the primer for subsequent strand displacement RCA amplification.

Figure 24:
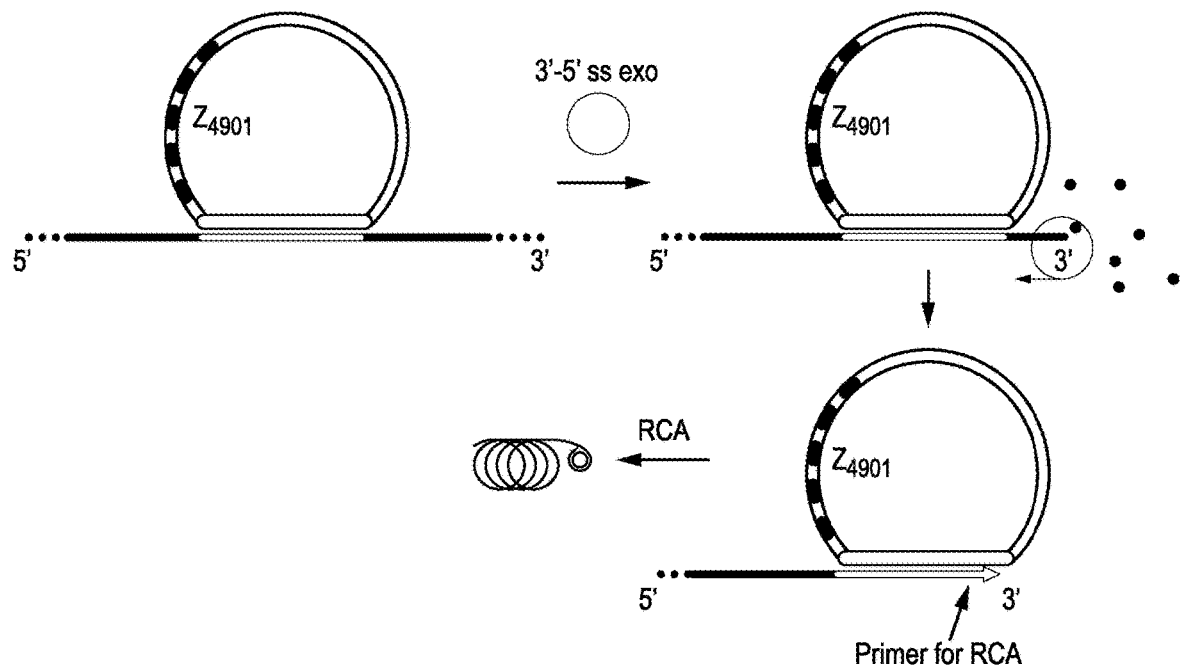
FIG. 24 is a schematic showing hybridization of a capture pair to a target sequence. A 3'-5' single stranded exonuclease (open circle) digests the target sequence until the target sequence is useful as a primer for RCA.

In the second example, as shown in FIG. 24, exonuclease activity is used to hydrolyze single stranded nucleotides from the 3'-end of the DNA target which is hybridized to a circle. After the DNA target and the pre-formed circle hybridize to each other, an enzyme with single strand-specific 3'-5' exonuclease activity is added to the reaction. The enzyme may be an exonuclease with the desired activity, such as Exonuclease I, Exonuclease T, or Mung Bean Nuclease. The enzyme may also be a DNA polymerase with 3'-5' exonuclease (proofreading) activity in the presence of one or more dNTPs, such as T4 DNA polymerase. The exonuclease digests the single stranded 3'-end of the DNA target until it reaches the portion that is hybridized to the pre-formed circle template. If an exonuclease is used, it will stop digestion once it reaches the double stranded region, thus leaving a 3'-end that can be extended by DNA polymerase during RCA (shown as the arrow). When a DNA polymerase and all four dNTPs are used, digestion will continue until the hybridized region of the template and circle is reached, but then primer extension will initiate at that point, and begin to copy the pre-formed circle sequence. Thus, the RCA reaction could also be initiated during this step. If this is not desirable, then fewer than four dNTPs can be used with a 3'-5' exonuclease, and extension will cease with the first missing dNTP.

In some instances, it may be desirable to amplify the number of circularized RCA targets relative to the number of input DNA targets. This might be done with an exponential amplification method such as PCR. However, in some cases, imprecision and target bias of exponential methods may interfere with downstream analysis. In applications such as fetal trisomy testing (non-invasive prenatal testing, or "NIPT"), very high precision and very low bias are required. Thus, linear amplification with inherently low bias can be used as described herein. Here, the steps of circularization for RCA with linear amplification can be combined. Optionally, during linear amplification, it may be desirable to limit, decrease, remove or inactivate the first primer prior to the cycling reaction.

Figure 25:
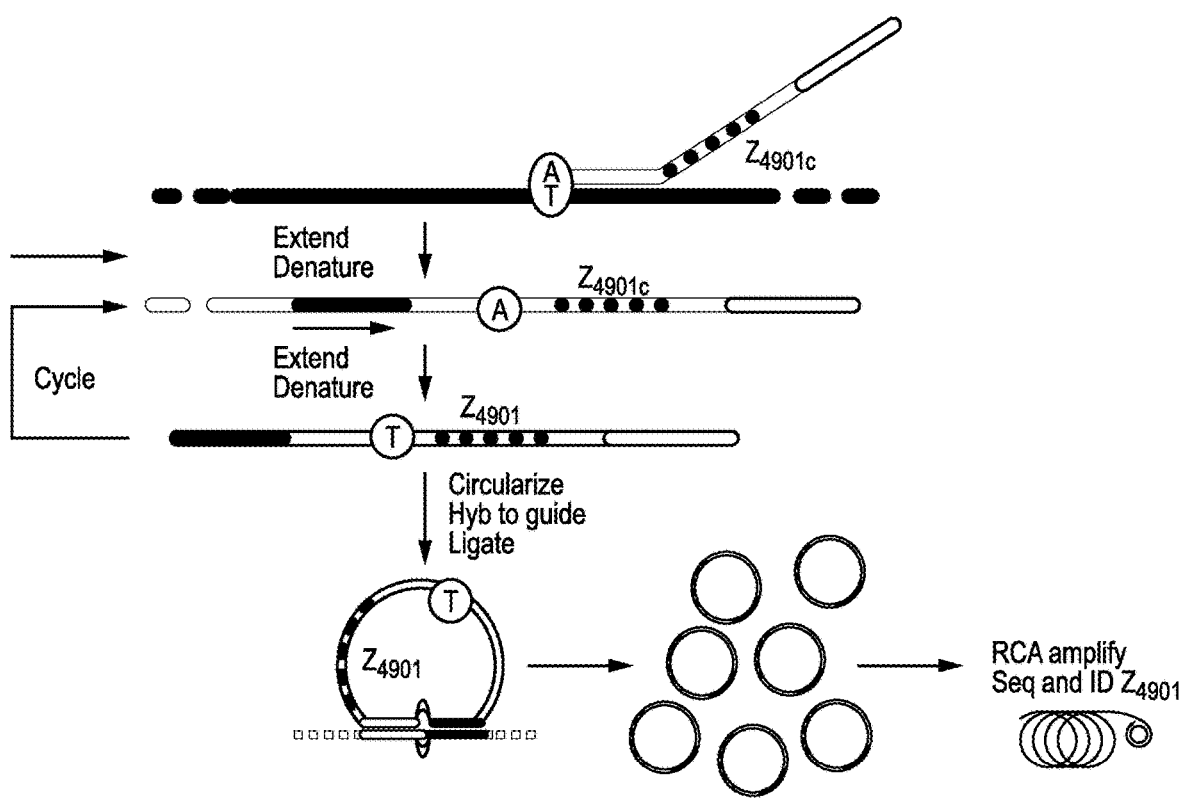
FIG. 25 is a schematic showing linear, sequence variant or SNP-dependent amplification. A primer containing a target hybridization region and one member of a capture pair is bound to a target including the sequence variant or SNP and is extended in the presence of a match. A second primer, which is also the second member of a capture pair, hybridizes to the extension product of the first primer, forming a complete circularization molecule with both members of a capture pair, the barcode and the variant. The two strands are denatured, allowing the binding pair of the second extension product to hybridize to a guide oligonucleotide and be ligated, thus forming a circular molecule that serves as an RCA amplification template. The denaturation and extension cycle can be repeated to linearly amplify the target sequence containing the SNP. The method can be used for low abundance targets for more accurate scoring. There is lower bias since amplification is linear instead of exponential.

As shown in FIG. 25, cycling primer extension is used and is similar to the method of constructing a circularization template by primer extension shown in FIG. 20. The difference is that after the first ligation that produces the first circle, which is detached from the target sequence in the sample nucleic acid by denaturing the sample, the second primer is extended again and ligated to form another circle. The cycles of extension, denaturation, and ligation are repeated as many times as desired. The circles produced are used as templates for RCA.

Figure 26:
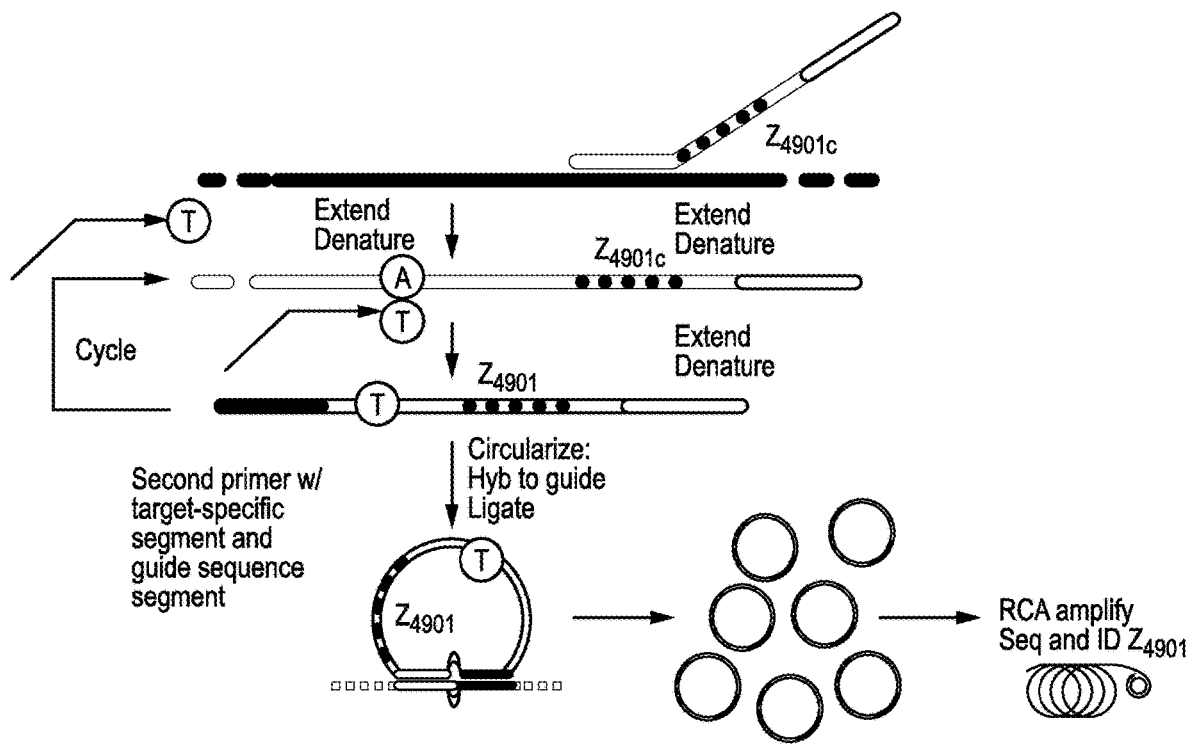
FIG. 26 is a schematic similar to the schematic in FIG. 25 with the exception that the second primer also includes a sequence complementary to a guide sequence used to facilitate ligation. The capture pair can be the same for any or all of the SNP or variant targets to be amplified, thus enabling use of fewer, or even a single guide sequence to facilitate ligation and circularization.

A variation of the cycling primer extension method is depicted in FIG. 26, in which the second primer is specific for a SNP position on the DNA target, and also contains a separate segment for hybridizing to a guide sequence during the ligation step. Here, the first primer may hybridize and extend all alleles of this DNA target, but the second primer gives specificity to the reaction since it will only extend if there is a match at the SNP position. In this example, the guide sequence segments can be the same for all targets, so only a single species of guide sequence need be present in the reaction.

Figure 27:
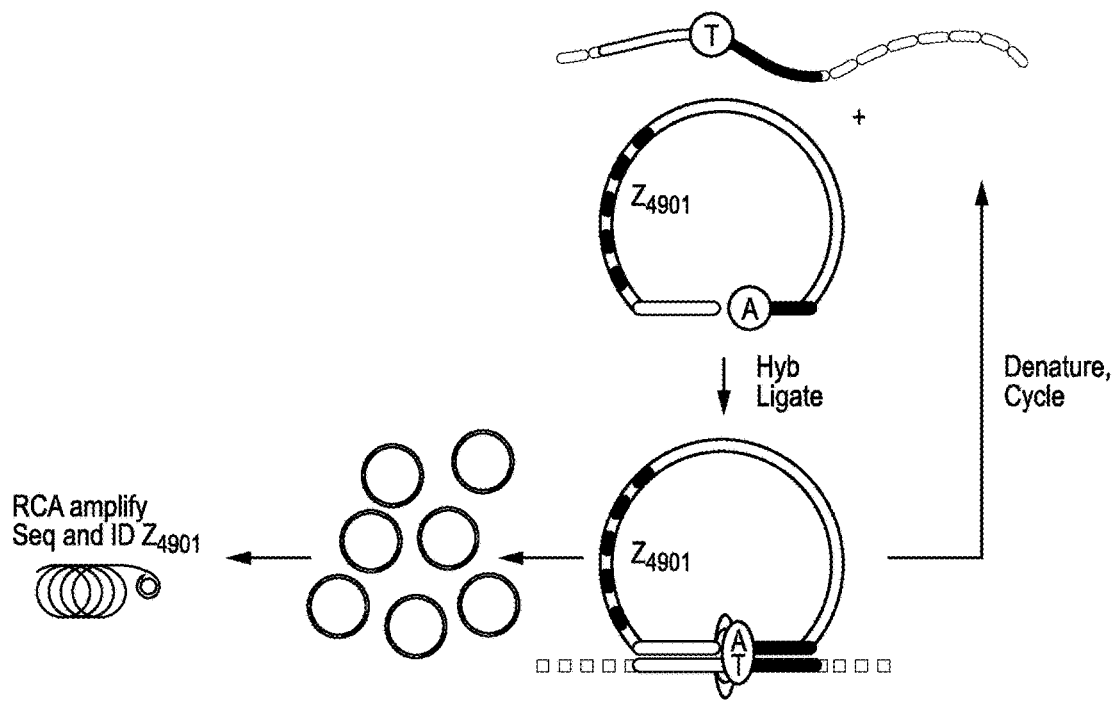
FIG. 27 is a schematic showing cycling, sequence variant or SNP-dependent ligation. After hybridization to a target sequence and ligation of a capture pair, the target molecules can be denatured and recycled to generate additional capture pairs. Linear amplification can be useful for low abundance targets for more accurate scoring. Accuracy is increased since each cycle is SNP-dependent. There is lower bias since non-exponential cycling circle ligation is used.

An additional example of cycling circle ligation is shown in FIG. 27. Circle templates are provided for each DNA target locus, with ends that can be ligated only when hybridized to a sequence exactly complementary to the DNA target. In this case, ligation is dependent on the presence of the correct SNP nucleotide in the target that matches the 3' or 5'-end of the Zip barcoded circle. After ligation, the completed circle and target are denatured, and another circle is hybridized and then ligated. In this example, if a circularization template with a different nucleotide at the SNP position (containing a different Zip barcode) is hybridized to the target, it won't be ligated, and therefore no product will be produced for sequencing. Any of the methods described herein for SNP or variant-specific circle formation may optionally be utilized to produce circles for amplification independent of the presence of SNPs or variant nucleotide sequences.

Figure 28:
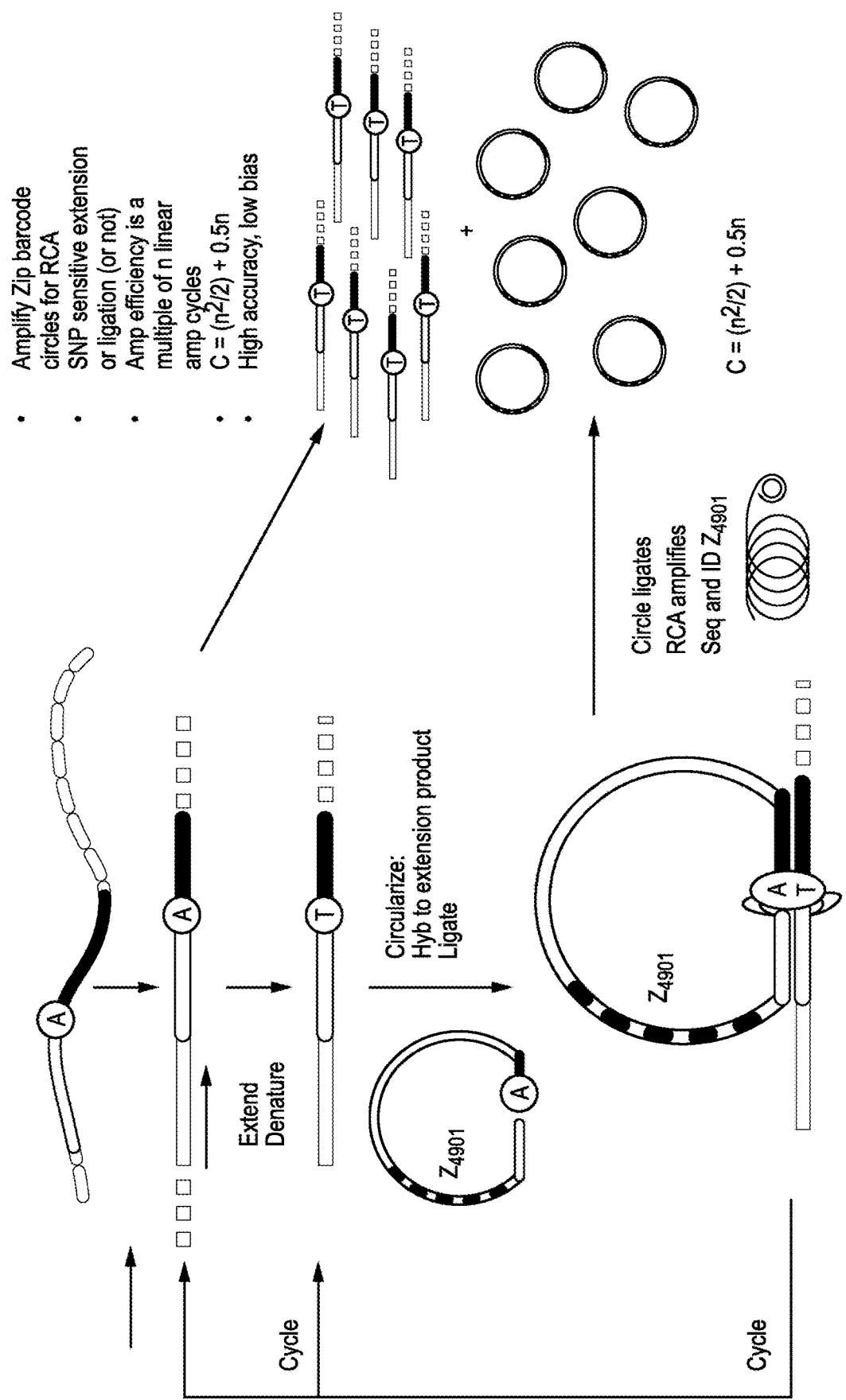
FIG. 28 is a schematic showing dual linear amplification of capture pairs including the barcode and sequence variant from the target to be used as templates for RCA. Linear primer extension and cycling ligation reactions similar to those depicted in FIGS. 26 and 27 occur simultaneously.
Figure 29:
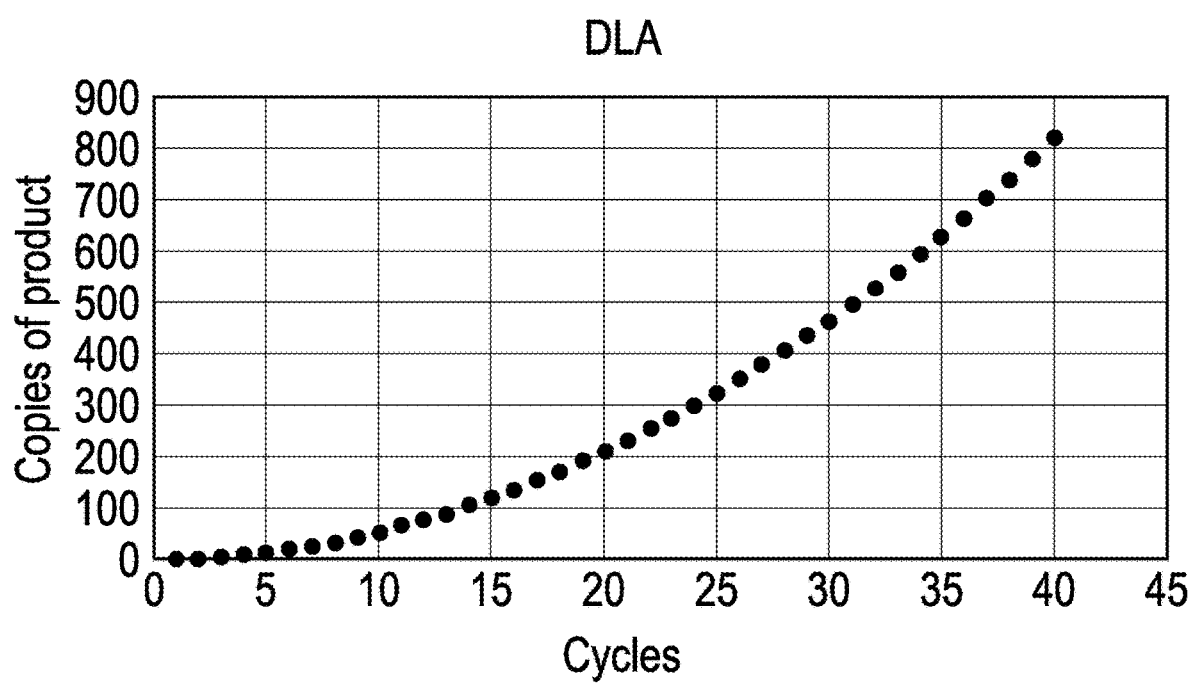
FIG. 29 is a graph showing the accumulation of products during dual linear amplification (DLA).

Combining both the cycling primer extension and cycling circle ligation into a single cycling reaction can result in a multiplicative linear amplification reaction, here called Dual Linear Amplification (DLA). One way to do this is shown in FIG. 28, in which primer extension is combined with SNP-dependent circle ligation. The primer extension product from the DNA target forms the guide sequence for ligating the circularization template. After extension, the duplex is denatured, then another primer anneals to the DNA target and the circle hybridizes to the primer extension product (acting as the guide sequence). The reaction is cycled in multiple steps of hybridization, extension and ligation. Extension products accumulate and serve as ligation guide sequences at each cycle. Circle products ("C") accumulate in n cycles according to the equation: $C=(n^2/2)+0.5n$.

Single linear amplifications accumulate n products in n cycles, but DLA is approximately multiplicative. After 5 cycles 15 copies of product accumulate, after 10 cycles 55 copies accumulate, and after 20 cycles 210 copies accumulate. The relationship between cycles and copies of product is shown in the following chart in FIG. 29 (assuming 100% efficiency at each cycle).

Example 1 demonstrates a procedure for synthesizing and sequencing picospheres, starting from circular DNA templates. Circular templates in accordance with the disclosed technique optionally include a sequence complementary to the sequencing primer, and a target-complementary sequence resulting from ligation of a capture pair specific for a target sequence. These features are illustrated in FIGS. 1-2. In the following demonstration, however, the circular ssDNA template was produced in the absence of a target sequence by intramolecular ligation of a synthetic ssDNA molecule. The sequence determined immediately downstream of the sequencing primer in this Example represented the Zip barcode sequence.

Example 1

Picosphere Sequencing on a Surface

Picospheres were prepared by rolling circle amplification (RCA) using a circularized single-stranded DNA oligonucleotide as a template. The 5'-phosphorylated single-stranded DNA oligonucleotide of SEQ ID NO:1 was circularized using thermostable CircLigase II ssDNA ligase (Epicentre; Madison, Wis.) under standard reaction conditions in a final volume of 20 μL. After incubating the reaction mixture at 60° C. for 1 hour, the enzyme was inactivated at 80° C. for 10 minutes. Rolling circle amplification was carried out using the circularized DNA template and the phi29 DNA polymerizing enzyme (Thermo Fisher; Waltham, Mass.) in a reaction buffer (33 mM Tris-acetate (pH 7.9), 10 mM magnesium acetate, 66 mM potassium acetate, 0.1% (v/v) Tween-20, 1 mM DTT), supplemented with 0.5 mM of all four dNTPs, 0.2 mg/mL BSA, and 1-5 μM of the RCA primer of SEQ ID NO:2. The reaction was incubated at 30° C. for 30 minutes to overnight, and then inactivated at 65° C. for 10 minutes. The resulting picospheres next served as templates in a sequencing-by-binding assay employing either a fluorescently labeled nucleotide or a fluorescently labeled polymerase.

Sequencing was carried out using a flow cell constructed to include a streptavidin-coated gold layer deposited on one surface of a glass prism, and total internal reflection fluorescence (TIRF) monitoring by microscopy. Picospheres were immobilized to the flow cell surface using a solution that included 10 mM Tris HCl (pH 7.9), 50 mM NaCl, 10 mM MgCl$_2$ and 1 mM DTT; together with 0-0.1 μM of a 5'-biotinylated sequencing primer (SEQ ID NO:3) complementary to a sequencing primer-hybridizing sequence within the RCA product. Following the immobilization step, a wash step removed non-bound material from the flow cell. Ternary complexes were then formed and detected by flowing in an examination buffer that included 50 μM Cy5-dCTP (Thermo Fisher; Waltham, Mass.), and 0.5 U/μL Bsu large fragment DNA polymerase (New England BioLabs; Ipswich, Mass.), under conditions that precluded an incorporation reaction (i.e., no divalent catalytic metal ion).

TABLE 1

Oligonucleotide Sequences

| | |
|---|---|
| ssDNA oligo-nucleotide | GTCCTCAGTCCCAAAAGTCTGGGCCTAGGGTGCTGCAG AGGCCCAGAGCTTCTTTTTTTTTTTCCGTCTGAAGAG GA (SEQ ID NO: 1) |
| RCA primer | CTTTTGGGACTGAGGAC (SEQ ID NO: 2) |
| Sequencing primer | GCTTCTTTTTTTTTTTCCGT (SEQ ID NO: 3) |

Two different examination buffer conditions were tested in the sequencing procedure. The first examination buffer further included 300 mM KCl, 20 mM Tris (pH 8), 0.01% (v/v) Tween-20 (called "300 mM KCl" buffer); and the second examination buffer included 1M KCl, 20 mM Tris (pH 8), 0.01% (v/v) Tween-20 (called "1M KCl" buffer). Detection of the fluorescently labeled nucleotide (i.e., Cy5-dCTP) indicated formation of a stabilized ternary complex that included: (1) the primed template nucleic acid (i.e., the picosphere hybridized to the sequencing primer); (2) the polymerase; and (3) the next correct nucleotide. This detection took place without any nucleotide incorporation (i.e., formation of a phosphodiester bond). Interactions between these three components were monitored using an Olympus fluorescence microscope (Olympus, Japan) equipped with 20× objective lens. The fluorescence channel was configured for detecting the Cy5 (650 nm excitation, 680 nm emission) label. Images were captured by QImaging QClick cooled CCD camera (QImaging, Canada), and a 300-millisecond exposure time. Localization of the fluorescent emission signal to the position of a picosphere in the flow cell (i.e., a nucleic acid feature) indicated ternary complex formation. The picosphere nucleotide sequence immediately downstream of the 3'-end of the sequencing primer represented the model Zip barcode sequence.

Results from the procedure clearly indicated distinguishable differences between peak signal values (i.e., maximum measured fluorescence) and background signals (i.e., off-target fluorescence) for the picospheres. This demonstrated that binding of the next correct nucleotide was easily detectable using the labeled nucleotide. Notably, the observed signal-to-noise ratio was about 50% higher when using the 300 mM KCl buffer compared to the 1 M KCl buffer. Detection of dCTP as the cognate nucleotide identified the first nucleotide of the model Zip barcode sequence.

Next, sequencing was demonstrated using fluorescently labeled Bsu-polymerase. Picospheres were re-suspended with 300 mM KCl buffer that included native, unlabeled dCTP in place of Cy5-dCTP of the procedure described immediately above; and further included fluorescently labeled Bsu polymerase in place of unlabeled Bsu polymerase. Picospheres were hybridized to the sensor surface as described above. Sequencing was carried out using an Olympus fluorescence microscope (Olympus, Japan) with 4× objective lens. The fluorescence channel was again configured for detection of the Cy5 label (650 nm excitation, 680 emission). The image was captured by QImaging QClick cooled CCD camera (QImaging, Canada) using a 300-millisecond exposure time.

Results of the procedures confirmed that binding of the next correct nucleotide was easily detected using the fluorescently labeled polymerase. More specifically, Cy5 fluorescence associated with picospheres was detected in the examination buffer. Upon shifting to incorporation conditions, the Cy5 signal disappeared. This confirmed that stabilized ternary complexes including the next correct nucleotide and the polymerase properly formed in the examination buffer, and that ternary complexes dissociated following incorporation of the correct nucleotide into the picosphere template.

These data collectively show that either fluorescently labeled dNTP or fluorescently labeled polymerase could be used for picosphere sequencing.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A method for identifying nucleotides in a template nucleic acid, comprising
   (a) providing a solid support comprising a template nucleic acid comprising a first region and a second region, wherein the template nucleic acid is hybridized to a first primer having a 3' match upstream of the first region, and wherein the template nucleic acid is hybridized to a second primer having a 3' mismatch upstream of the second region;
   (b) after step (a), forming a first stabilized ternary complex that comprises the template nucleic acid hybridized to the first primer, a polymerase and a first cognate nucleotide, wherein the 3' mismatch prevents the second primer from forming a stabilized ternary complex;
   (c) after steps (a) and (b), detecting the first stabilized ternary complex to identify the first cognate nucleotide, wherein formation and detection occurs without incorporation of the first cognate nucleotide into the first primer, and wherein the first primer comprises a terminal nucleotide with a chemical modification that inhibits incorporation;
   (d) after steps (a)-(c), removing the 3' mismatch from the second primer;
   (e) after steps (a)-(d) after step (d), forming a second stabilized ternary complex comprising the template nucleic acid hybridized to the second primer, a polymerase and a second cognate nucleotide; and
   after steps (a)-(e), detecting the second stabilized ternary complex to identify the second cognate nucleotide, wherein formation and detection occurs without incorporation of the second cognate nucleotide into the second primer, and wherein the second primer comprises a terminal nucleotide with a chemical modification that inhibits incorporation.

2. The method of claim 1, wherein the template nucleic acid comprises a concatemer of target sequences.

3. The method of claim 1, wherein the template nucleic acid is covalently attached to the solid support.

4. The method of claim 1, wherein the template nucleic acid is attached to the solid support via hybridization a primer.

5. The method of claim 1, wherein the second cognate nucleotide complements a base in a barcode sequence.

6. The method of claim 5, wherein the first cognate nucleotide complements a sequence variant in a target sequence.

7. The method of claim 1, wherein the first cognate nucleotide comprises a label that is detected in step (c).

8. The method of claim 1, wherein the second cognate nucleotide comprises a label that is detected in step (f).

9. The method of claim 1, wherein the chemical modification on the first primer comprises a reversible blocking moiety.

10. The method of claim 9, wherein step (c) further comprises (ii) deblocking the first primer and (iii) adding a reversibly terminated nucleotide to the deblocked primer, thereby producing a reversibly terminated, extended primer.

11. The method of claim 1, further comprising, prior to step (d), incorporating the first cognate nucleotide into the primer.

12. The method of claim 11, wherein the chemical modification on the second primer comprises a reversible blocking moiety.

13. The method of claim 12, wherein step (f) further comprises (ii) deblocking the second primer and (iii) adding a reversibly terminated nucleotide to the deblocked second primer, thereby producing a reversibly terminated, extended, second primer.

14. The method of claim 1, further comprising, after step (f), incorporating the second cognate nucleotide into the primer.

15. The method of claim 1, wherein the polymerase in the first stabilized ternary complex comprises a label that is detected in step (c).

16. The method of claim 1, wherein the polymerase in the second stabilized ternary complex comprises a label that is detected in step (f).

17. The method of claim 1, wherein step (d) comprises removing the 3' mismatch from the second primer using a polymerase with a 3'-5' exonuclease activity.

18. The method of claim 1, wherein a non-naturally occurring nucleotide is present at the 3' end of the second primer.

19. The method of claim 1, further comprising, prior to step (d), replacing the first cognate nucleotide with a nucleotide that is incorporated into the primer.

20. The method of claim 1, further comprising, after step (f), replacing the second cognate nucleotide with a nucleotide that is incorporated into the primer.

* * * * *

UNITED STATES PATENT AND TRADEMARK OFFICE
CERTIFICATE OF CORRECTION

PATENT NO. : 11,326,206 B2
APPLICATION NO. : 16/091969
DATED : May 10, 2022
INVENTOR(S) : Yi Zhang et al.

It is certified that error appears in the above-identified patent and that said Letters Patent is hereby corrected as shown below:

In the Claims

Claim 1, Column 42, Line 40:
Replace "after steps (a)-(e), detecting the second stabilized ternary" with --(f) after steps (a)-(e), detecting the second stabilized ternary--

Signed and Sealed this
Twenty-seventh Day of September, 2022

Katherine Kelly Vidal
*Director of the United States Patent and Trademark Office*